(12) United States Patent
Cripps et al.

(10) Patent No.: US 7,517,533 B2
(45) Date of Patent: Apr. 14, 2009

(54) PSEUDOMONAS AERUGINOSA ANTIGENS

(75) Inventors: Allan W. Cripps, Nicholls (AU); Jennelle M. Kyd, McKellar (AU); Linda D. Thomas, Aranda (AU)

(73) Assignee: The University of Canberra, Belconnen (AU)

( * ) Notice: Subject to any disclaimer, the term of this patent is extended or adjusted under 35 U.S.C. 154(b) by 734 days.

(21) Appl. No.: 10/148,414

(22) PCT Filed: Dec. 4, 2000

(86) PCT No.: PCT/GB00/04625

§ 371 (c)(1),
(2), (4) Date: Dec. 2, 2002

(87) PCT Pub. No.: WO01/40473

PCT Pub. Date: Jun. 7, 2001

(65) Prior Publication Data

US 2004/0071713 A1    Apr. 15, 2004

(30) Foreign Application Priority Data

Dec. 3, 1999  (GB) ................................. 9928676.7

(51) Int. Cl.
*A61K 39/02* (2006.01)
*A61K 39/00* (2006.01)
*A61K 39/108* (2006.01)
*A61K 38/00* (2006.01)
*A61K 38/16* (2006.01)
*A01N 37/08* (2006.01)

(52) U.S. Cl. ............. 424/260.1; 424/234.1; 424/190.1; 424/184.1; 514/2; 530/350; 530/300; 530/825; 530/806

(58) Field of Classification Search ................. 530/350, 530/300, 825, 806; 424/234.1, 260.1, 190.1, 424/93.47, 184.1; 514/2
See application file for complete search history.

(56) References Cited

U.S. PATENT DOCUMENTS

| | | | |
|---|---|---|---|
| 5,554,372 A * | 9/1996 | Hunter | 424/280.1 |
| 6,248,551 B1 * | 6/2001 | De Reuse et al. | 435/18 |
| 6,551,795 B1 * | 4/2003 | Rubenfield et al. | 435/69.1 |
| 2004/0033234 A1 * | 2/2004 | Berinstein et al. | 424/185.1 |

FOREIGN PATENT DOCUMENTS

WO    WO 98/32769    7/1998

OTHER PUBLICATIONS

Wilson et al. J. Bacteriol. 177: 3052-3057, 1995.*
Soubrier et al. Gene 116: 99-104, 1992.*
Farnaud et al. Biochem. J. 340: 711-714, 1999.*
Brammar et al. FEBS Lett. 215: 291-294, 1987.*
Clarke PH. In: Microorganisms as Model System for Studying Evolution. (Ed) Mortlock RP. Plenum, New York, pp. 187-231, 1984.*
Cripps et al. Behring Inst. Mitt., 98: 262-268, 1997.*
Altschul, S.F., et al., "Gapped BLAST and PSI-BLAST: a new generation of protein database search programs," *Nucleic Acids Res.* 25:3389-3402, Oxford University Press (1997).
Ambler, R.P., et al., "The amino acid sequence of the aliphatic amidase from *Pseudomonas aeruginosa*," *FEBS Lett.* 215:285-290, Federation of European Biochemical Societies (1987).
EMBL Nucleotide Sequence Database, Accession No. AE 004642, Stover, C.K., et al., European Bioinformatics Institute (Sep. 2000).
EMBL Nucleotide Sequence Database, Accession No. AE004747, Stover, C.K., et al., European Bioinformatics Institute (Sep. 2000).
Stanislavsky, E.S., and Lam, J.S., "*Pseudomonas aeruginosa* antigens as potential vaccines," *FEMS Microbiol. Rev.* 21:243-277, Federation of European Microbiological Societies (1997).
Stover, C.K., et al., "Complete genome sequence of *Pseudomonas aeruginosa* PAO1, an opportunistic pathogen," *Nature* 406:959-964, Nature Publishing Co. (Aug. 2000).
International Search Report for International Application PCT/GB 00/04625, mailed Aug. 14, 2001. European Patent Office, Netherlands.

* cited by examiner

*Primary Examiner*—S. Devi
(74) *Attorney, Agent, or Firm*—Sterne, Kessler, Goldstein & Fox P.L.L.C.

(57) ABSTRACT

Proteins derived from *Pseudomonas aeruginosa* are antigenic and are of use in the treatment, prophylaxis and diagnosis of *P. aeruginosa* infection.

5 Claims, 7 Drawing Sheets

Elution profile of *P. aeruginosa* proteins from crude Zwittergent extracts by anion exchange chromatography. The first peak is the unbound fraction. 'A' represents the programmed NaCl gradient, 'B', the actual NaCl gradient and 'C' represents the absorbance at 280nm. Arrows represent separate protein peaks.

FIG. 2

SDS-PAGE analysis of peak fractions from anion exchange chromatography of the crude Zwittergent extract of *P. aeruginosa*. Corresponding fractions from successive chromatography runs were pooled. Protein was separated on a gradient 10-15% polyacrylamide gel and Coomassie stained. Lanes: 1, molecular mass standards (values in kDa on left); 2, peak one; 3, peak two; 4, peak three; 5, peak four; 6, peak five; 7, peak six; 8, peak seven.

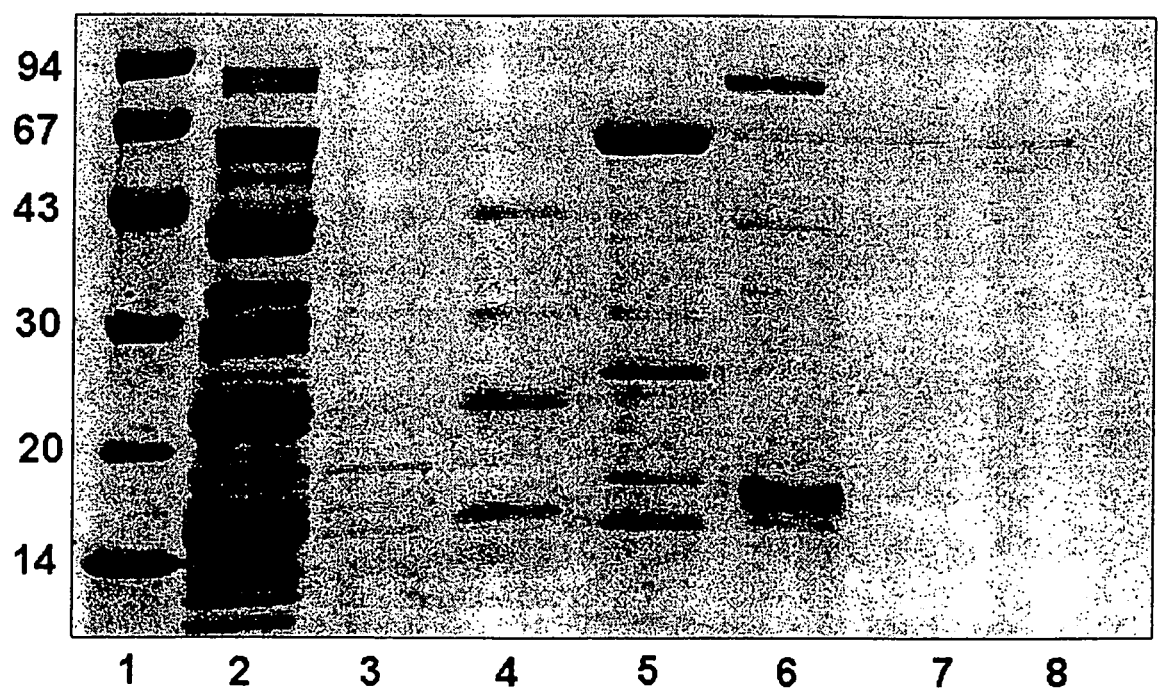

SDS-PAGE analysis of purified P.aeruginosa antigens.
Lanes: 1. Milecular mass standards with mass expressed in kDa on vertical scale. 2. *Pa* 13; 3. *Pa* 20 (ACP); 4. *Pa* 40 (amidase); 5. *Pa* 45; 6. *Pa* 80.

Western blot demonstrating recognition of Pa80 in the *P. aeruginosa* (strain 385) cell lysate by antigen-specific antisera. Lanes (1) molecular weight markers (2) Anti-*Pa*80 rat serum recognition of a 80 kDa band in the *P. aeruginosa* crude cell lysate Dot blot of *P. aeruginosa* 385 (serotype 2) cell lysate demonstrating recognition of *Pa*80 by antigen-specific antisera.

Detection of antigen-specific antibody (IgG) binding to P.aeruginosa proteins. Curve 1 represents negative binding by non-immune serum and Curve 2 shows detection of fluorescence following binding by protein antisera. A:anti-Pa13; B:anti-Pa20 (ACP); C:anti-Pa40 (amidase); D anti-Pa45; E: anti-Pa80

FIG. 7

Pa40 - DNA and translated amino acid sequence (from Pa385)

```
1/1                                                                31/11                                                               61/21
CGT CAC GGC GAT ATT TCC AGC AAC GAC AGC GTC GGA GTG GCG GTC AAC TAC AAG ATG CCG CGC CTG CAC ACC GCG GCG GAG GTC
 R   H   G   D   I   S   S   N   D   S   V   G   V   A   V   N   Y   K   M   P   R   L   H   T   A   A   E   V
91/31                                                              121/41                                                             151/51
CTG GAC AAC GCC CGG AAG ATC GCC GAG ATG GTC AAG CAG GGC ATG GAC CTG CCC GGC GTG TTC CCC GAG TAC AGC
 L   D   N   A   R   K   I   A   E   M   V   K   Q   G   M   D   L   P   G   V   F   P   E   Y   S
181/61                                                             211/71                                                             241/81
CTG CAG GGC ATC ATG TAC GAT CCG GCG GAG ATG GAA ACC GAA ACC GCC ATC CCC GGC GAG GAA ACC TTC TCC CGC GCC TGC
 L   Q   G   I   M   Y   D   P   A   E   M   E   T   E   T   A   I   P   G   E   E   T   F   S   R   A   C
271/91                                                             301/101                                                            331/111
CGC AAG GCC AAC GTC TGG GGC GTA TTC TCC CTC ACC GGC GAA CGG CAC CGG CCG CGC AAG GCC CCG TAC AAC ACC CTG GTG CTG
 R   K   A   N   V   W   G   V   F   S   L   T   G   E   R   H   R   P   R   K   A   P   Y   N   T   L   V   L
361/121                                                            391/131                                                            421/141
ATC GAC AAC GGC GAG ATC GTC CAG AAG TAC CGC AAG ATC ATT CCC TGG TGC CCC ATC GAG GGC TGG TAT CCC CAG ACC TAC
 I   D   N   G   E   I   V   Q   K   Y   R   K   I   I   P   W   C   P   I   E   G   W   Y   P   Q   T   Y
451/151                                                            481/161                                                            511/171
GTC AGC GAA GGG CCG AAG ATG AAG ATC ATC AGC CTG ATC ATC TGC GAC GAC GGC AAC TAC CCG GAA ATC TGG GCC GCG ATG AAG
 V   S   E   G   P   K   M   K   I   I   S   L   I   I   C   D   D   G   N   Y   P   E   I   W   A   A   M   K
541/181                                                            571/191                                                            601/201
GGC GCC GAG CTG ATC GTG CGC TGC CAG GGC TAC ATG GTG AAG GAC CAG AAG GAC GTG ATG ATG GCC TGG GCC AAC
 G   A   E   L   I   V   R   C   Q   G   Y   M   V   K   D   Q   K   D   V   M   M   A   W   A   N
631/211                                                            661/221                                                            691/231
AAC TGC TAT GTG GCG GTG GCC AAC GCC GCC GGT TTC GAC GGC GTG TAT TCC TAC TTC GGC CAC TCG GCG ATC ATC GGC TTC GAC GGT CGT
 N   C   Y   V   A   V   A   N   A   A   G   F   D   G   V   Y   S   Y   F   G   H   S   A   I   I   G   F   D   G   R
721/241                                                            751/251                                                            781/261
ACC CTC GGT GAG TGC GGC GAG GAG ATG GGT ATC CAG CTG CAG CTG TCG CTT TCG CAG ATC CGG GAT GCG GCC CGG CTG GCC AAC GAT CAG
 T   L   G   E   C   G   E   E   M   G   I   Q   L   Q   L   S   L   S   Q   I   R   D   A   A   R   L   A   N   D   Q
811/271                                                            841/281                                                            871/291
AGC CAG AAC CAC CTC TTC AAG ATC CTC CAC CGC GGC TAC AGC GGC TTG CAG GCG TCC GGC GAC GAT GGC GAC CGG GAC TCC GCG GAG TGT CCG
 S   Q   N   H   L   F   K   I   L   H   R   G   Y   S   G   L   Q   A   S   G   D   D   G   D   R   D   S   A   E   C   P
901/301                                                            931/311                                                            961/321
TCG CAG TTC TAC CGC ACC TGG GTC ACC GAC AAT GCG GAG AAG GCG AAG GCG CGC GAG AAT GTC GAG CGA TGC ACC CGC TCG ACT ACC GTG GCG CAA
 S   Q   F   Y   R   T   W   V   T   D   N   A   E   K   A   K   A   R   E   N   V   E   R   C   T   R   S   T   T   V   A   Q
991/331                                                           1021/341
TGC CCG GTC GGC CGG CTG CCC TAC GAG GGA CTG GAG AAG GAG GCC
 C   P   V   G   R   L   P   Y   E   G   L   E   K   E   A
```

FIG. 8

Pa45 - DNA and translated amino acid sequence (from Pa385)

```
1/1                                                                                              61/21
CGC GCA GAA CTC AAC CAG GGC CTG GTC GAT TTC CTC AAG GCC TCG CCC ACG CCT TTC CAT GCT ACC GCC AGC CTC GCC CGC CTG GAA
 R   A   E   L   N   Q   G   L   V   D   F   L   K   A   S   P   T   P   F   H   A   T   A   S   L   A   R   L   E
91/31                                                                                            151/51
GCC GCC GGC TAC CGC CGC CTC GAC GAG CGC GAC GCC TGG CAC GAA GGC CGC TAC TAC GTG ACC TCG GTC TCG CTG
 A   A   G   Y   R   R   L   D   E   R   D   A   W   H   E   G   R   Y   Y   V   T   V   S   S   L
181/61                                                                                           241/81
ATC GCC ATC CGC CTG GGT CGT CGC TCG CCC CTG GAA AGC GGC TTC CGC GTC GGC TTC CAC AGC ACC GAC AGC GTC AAG
 I   A   I   R   L   G   R   R   S   P   L   E   S   G   F   R   V   G   F   H   T   D   S   V   K
271/91                                                                                           331/111
CCG AAC CCG GAG ATC GCT CGC AAC GGC TTC CTC CAG CTC CAG GTC GAA GTC TAT GGC GGC GCC CTC TTC GAC CGC GAC
 P   N   P   E   I   A   R   N   G   F   L   Q   L   Q   V   E   V   Y   G   G   A   L   F   D   R   D
361/121                                                                                          421/141
CTG TCA CTG GCC GGG CGC GTC ACC TTC CGC GCC AAT GGC AAG CTG GAA AGC CGC CTG GTC GCC AAG CGC GTA ATC CCC
 L   S   L   A   G   R   V   T   F   R   A   N   G   K   L   E   S   R   L   V   A   K   R   V   I   P
451/151                                                                                          511/171
AAC CTG GCC ATC CAT CTC AAC CGC GCC GCC GGT TGG CCG ATC AAC GAG CAG CGC CAG GAC TTC GAC GTG CTG CTG GCG
 N   L   A   I   H   L   N   R   A   A   G   W   P   I   N   E   Q   R   Q   D   F   D   V   L   L   A
541/181                                                                                          601/201
CCG GGC GAG GCC TTC CGC GAC CTG CTC GAA CAG GAA CTC GGT CTC GAC GAG TTC ATC GCC GAC CTG CTG GAC TAC GAG
 P   G   E   A   F   R   D   L   L   E   Q   E   L   G   L   D   E   F   I   A   D   L   L   D   Y   E
631/211                                                                                          691/231
CTG TCG TTC TAC GAC ACC CAG TCC GCC GCG GTG GTA GCG GCC GAC GGC GAC GAG AAC TGC CGG CCG ATC CAG CGC TGC
 L   S   F   Y   D   T   Q   S   A   A   V   V   A   A   D   G   D   E   N   C   R   P   I   Q   R   C
721/241                                                                                          781/261
CAC GCC GGC CTG GAA CTG GAA AGC GGC GAC CTG CGC CGC AAC TAC AGC GAA ACC GAG GAC CAC TTC AGC CGG CCG TCC TGT TCG
 H   A   G   L   E   L   E   S   G   D   L   R   R   N   Y   S   E   T   D   H   F   S   R   R   P   C   S
811/271                                                                                          871/291
CAT TGC GGC GCC GAC GTA GAA CAG CAG CTG CCG GGC ATC ACC ATC ATC GGC GAC GCG GAC GGC GAC GCA TTC GAA GGC TCG
 H   C   G   A   D   V   E   Q   Q   L   P   G   I   T   I   I   G   D   A   D   G   D   A   F   E   G   S
901/301                                                                                          961/321
CTG CTG GTC TCG GCC GAC AAC GCC CAT GGC GAC AAG CAC GAC AAC CAT GGC CCG AAC CAG CGC
 L   L   V   S   A   D   N   A   H   G   D   K   H   D   N   H   G   P   N   Q   R   S
991/331                                                                                          1051/351
CCG GTG ATC AAG ATC AAC AGC TAT GCC ACC AAC GCC CAC CTC TGC CAG GAC AGC GAA GTG
 P   V   I   K   I   N   S   Y   A   T   N   A   H   L   C   Q   D   S   E   V
1081/361                                                                                         1141/381
CCG GTG CAG AGC TTC GTG CCG CTG CCG GGC ATG TGC ACC GGC ATC TCC TGT TCG
 P   V   Q   S   F   V   A   T   R   A   T   G   I   C   C   S
1171/391                                                                                         1231/411
GAC ATA GGC CTG CCG ACC TTC GCC ATG CAC CGC ATT CGC GAG CTG GCC CAC GAC CTG GCG CAC GTG CTC GGC GCC
 D   I   G   L   P   T   F   A   M   H   R   I   R   E   L   A   H   D   L   A   H   V   L   G   A
1261/421
TTC TAC GCC AGC AGC GAG CTG CCC
 F   Y   A   S   S   E   L   P
```

PSEUDOMONAS AERUGINOSA ANTIGENS

CROSS REFERENCE TO RELATED APPLICATIONS

The present application is the U.S. national stage of International Application No. PCT/GB00/04625, filed 4 Dec. 2000, which was published under PCT Article 21(2) in English.

BACKGROUND OF THE INVENTION

1. Field of the Invention

The present application relates to antigenic proteins which are derived from *Pseudomonas aeruginosa* and to the use of these proteins in medicine, particularly in the treatment, prophylaxis and diagnosis of *Pseudomonas aeruginosa* infection.

2. Related Art

*P. aeruginosa* is a Gram-negative aerobic motile bacterium. It is an environmentally ubiquitous, extracellular, opportunistic pathogen that causes significant morbidity and mortality in immuno-compromised subjects. Infection is of particular significance in subjects with cystic fibrosis, burns, chronic bronchitis, bronchiectasis and cancer.

The genome of *P. aeruginosa* has recently been sequenced and details of the project have been placed on the internet (www.*pseudomonas*.com). However, at the priority date of the present invention, the information was not complete and had not been verified. This information is now complete and has been verified.

Identification of immune responses, the search for vaccine candidates and suitable components for diagnostic tests have focused on the outer membrane components of *P. aeruginosa*. The outer membrane of *P. aeruginosa* contains toxins, including the lipopolysaccharide endotoxin, phospholipid and outer membrane proteins (OMPs).

The various outer membrane proteins (OMPs) of *P. aeruginosa* have been assigned an alphabetical naming system. While several proteins have been characterised by this scheme, the expression of some is only transient and highly dependent upon nutrient availability, culture conditions and the presence of antibiotic. Presently, three major OMPs, designated F, H2 and I, are recognised as antigenically common to, and expressed in high copy numbers, in all strains of *P. aeruginosa*.

BRIEF SUMMARY OF THE INVENTION

The present inventors have employed protein purification methods to isolate homogenous preparations of both OMPs and cytosolic proteins. Using a method of ZWITTERGENT® extraction with modifications to liquid column chromatography and gel electrophoresis steps, several proteins have been purified, identified and assessed for their vaccine potential. The proteins were denoted by their molecular mass and their identity confirmed by amino-terminal sequencing.

The inventors have isolated and identified proteins from a preparation of *P. aeruginosa*. These proteins are designated Pa13, Pa20 (ACP), Pa 40 (amidase), Pa45 and Pa80. Amino-terminal sequences have been obtained for Pa13, Pa20 (ACP), Pa40 (amidase), Pa45 and Pa80. Following sequence analysis, the data obtained was subjected to a search using the BLAST (Basic Local Alignment Search Tool, the National Center for Biotechnology Information, Bethesda, Md., USA, Altschul et al, *Nucleic Acids Research,* 25 3389-3402 (1997)). Pa20 was ascribed as ACP because it had homology with a protein from *Pseudomonas syringae* and *P. aeruginosa*. Pa40 had homology with a known *P. aeruginosa* aliphatic amidase. The proteins designated Pa13, Pa45 and Pa80 were not found following this search.

DETAILED DESCRIPTION OF THE INVENTION

Therefore, in a first aspect of the present invention, there is provided a protein derived from *Pseudomonas aeruginosa*, wherein the protein has a molecular weight of about 13 kDa as determined by SDS PAGE under reducing conditions and has the following amino terminal sequence:

```
                                    (SEQ ID NO: 1)
A   E   T   I   V   N   T   T   K   A
Ala Glu Thr Ile Val Asn Thr Thr Lys Ala;
``` or an antigenic fragment or a homologue thereof.

In the second aspect of the present invention, there is provided a protein derived from *Pseudomonas aeruginosa*, wherein the protein has a molecular weight of about 45 kDa as determined by SDS PAGE under reducing conditions and has the following amino terminal sequence:

```
M   R   A   E   L   N   Q   G   L   I   D   F   L   K   A
Met Arg Ala Glu Leu Asn Gln Gly Leu Ile Asp Phe Leu Lys Ala  (SEQ ID NO: 2)
``` or an antigenic fragment or a homologue thereof.

In a third aspect of the invention, there is provided a protein derived from *Pseudomonas aeruginosa*, wherein the protein has a molecular weight of about 80 kDa as determined by SDS PAGE under reducing conditions and has the following amino terminal sequence:

```
M   S   E   Q   N   N   E   Q   R   S   Q   A   A
Met Ser Glu Gln Asn Asn Glu Gln Arg Ser Gln Ala Ala  (SEQ ID NO: 3)
``` or an antigenic fragment or a homologue thereof.

The skilled person will appreciate that homologues or derivatives of the proteins or polypeptides of the invention will also find use in the context of the present invention, i.e. as antigenic/immunogenic material. Thus, for instance proteins or polypeptides which include one or more additions, deletions, substitutions or the like are encompassed by the present invention. In addition, it may be possible to replace one amino acid with another of similar "type". For instance replacing one hydrophobic amino acid with another. One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention.

For the purposes of the present invention, a protein sequence may be regarded as substantially homologous to another protein sequence if a significant number of the constituent amino acids exhibit homology when using the one of the algorithms mentioned above. At least 40%, 50%, 60%, 70%, 80%, 90%, 95% or even 99%, in increasing order of preference, of the amino acids, may be homologous.

In this specification, the molecular weights of the proteins have been measured by SDS-PAGE under reducing conditions. As one skilled in the art will appreciate, the molecular weight values obtained by this method are accurate only to a degree of about ±10%.

As discussed herein, the protein of the invention is useful as antigenic material. Such material can be "antigenic" and/or "immunogenic". Generally, "antigenic" is taken to mean that the protein is capable of being used to raise antibodies or indeed is capable of inducing an antibody response in a subject. "Immunogenic" is taken to mean that the protein is capable of eliciting a protective immune response in a subject. Thus, in the latter case, the protein may be capable of not only generating an antibody response but, in addition, non-antibody based immune responses.

The proteins of the first, second and third aspects may be obtained by extraction from *P. aeruginosa* and, therefore, in a further aspect of the invention, there is provided a process for the preparation of an isolated and purified protein the process comprising the following steps:
(a) preparing cultures of *P. aeruginosa*, growing the cultures under appropriate conditions and harvesting them, followed by washing with centrifugation to yield a washed cell pellet;
(b) resuspending the washed cells in an appropriate buffer followed by disruption of the cells;
(c) centrifuging to remove cell debris and obtaining the supernatant containing soluble cell proteins;
(d) subjecting the solution obtained to anion exchange chromatography with a sodium chloride gradient elution, and pooling the fractions corresponding to each separate peak;
(e) purifying protein fractions by SDS-PAGE using a 10% T-1.42% C acrylamide-N,N-methylenebisacrylamide separating gel with a 4% T-0.36% C acrylamide-N,N-methylenebisacrylamide stacking gel polymerised in a 28 mm (internal diameter) column, run using 1% (w/v) SDS, 0.025M Tris, 0.2 M glycine buffer pH 8.3 in the upper and lower chambers at 40 mA and 10 W for 14 hours and eluting the proteins using a buffer of 0.025 M Tris, pH 8.3 and 6 ml fractions collected at flow rate of 1 ml/min;
(f) selecting a fraction containing a protein having a molecular weight of 13 kDa, 45 kDa or 80 kDa and isolating the protein from the selected fraction.

Alternatively, the proteins may be prepared by expressing the appropriate DNA.

Therefore, in a further aspect of the present invention there is provided a recombinant or isolated nucleic acid encoding a protein of the first, second or third aspects of the invention or nucleic acid complementary thereto.

For the purposes of expression, the nucleic acid, which may be DNA, may be inserted into a vector, which may be a plasmid, cosmid or a phage. The vector may be incorporated into the genome of a host organism, which may be either a prokaryotic or a eukaryotic organism.

The nucleic acid or a vector containing the nucleic acid, may be suitable for expressing the proteins of the present invention in a subject to be treated, i.e. it may be in the form of a DNA vaccine. Methods and agents suitable for the preparation of a DNA vaccine are well known to the skilled person.

As well as the proteins mentioned above, the inventors have isolated and purified further *P. aeruginosa* proteins. Several of these proteins have been found to be antigenic and are therefore likely to be of use in a method for the treatment or prophylaxis of *P. aeruginosa* infection, the method comprising administering to a patient in need of such treatment an effective amount of one of the proteins, or an antigenic fraction thereof.

The proteins are also useful for diagnosing *P. aeruginosa* infection.

Therefore, in a further aspect of the present invention, there is provided a protein or a nucleic acid encoding the protein, for use in medicine, particularly in the treatment, prophylaxis or diagnosis of infection by *P. aeruginosa*, wherein the protein is derived from *P. aeruginosa* and either.

i) has a molecular weight of about 13 kDa as determined by SDS PAGE under reducing conditions and has the following amino terminal sequence:

```
                                         (SEQ ID NO: 1)
    A   E   T   I   V   N   T   T   K   A
    Ala Glu Thr Ile Val Asn Thr Thr Lys Ala
```

Or an antigenic fragment or a homologue thereof; or ii) has a molecular weight of about 20 kDa as determined by SDS PAGE under reducing conditions and has the following amino terminal sequence:

```
    S   T   I   E   E   R   V   K   K   I   V   A   E   Q   L
    Ser Thr Ile Glu Glu Arg Val Lys Lys Ile Val Ala Glu Gln Leu or (SEQ ID NO: 4)
``` or an antigenic fragment or a homologue thereof; or iii) has a molecular weight of about 40 kDa as determined by SDS PAGE under reducing conditions and has the following amino terminal sequence:

```
    M   R   H   G   D   I   S   S   S   N   D   T   V   G
    Met Arg His Gly Asp Ile Ser Ser Ser Asn Asp Thr Val Gly  (SEQ ID NO: 5)
``` or an antigenic fragment or a homologue thereof; or iv) has a molecular weight of about 45 kDa as determined by SDS PAGE under reducing conditions and has the following amino terminal sequence:

```
M    R    A    E    L    N    Q    G    L    I    D    F    L    K    A
Met  Arg  Ala  Glu  Leu  Asn  Gln  Gly  Leu  Ile  Asp  Phe  Leu  Lys  Ala   (SEQ ID NO: 2)
``` or an antigenic fragment or a homologue thereof;

v) has a molecular weight of about 80 kDa as determined by SDS PAGE under reducing conditions; and has the following amino terminal sequence:

```
M    S    E    Q    N    N    E    Q    R    S    Q    A    A
Met  Ser  Glu  Gln  Asn  Asn  Glu  Gln  Arg  Ser  Gln  Ala  Ala   (SEQ ID NO: 3)
``` or an antigenic fragment or a homologue thereof.

Proteins may be obtained by extraction from *P. aeruginosa* and, therefore, in a further aspect of the invention, there is provided a process for the preparation of an isolated and purified protein, the process comprising the following steps:

(a) preparing cultures of *P. aeruginosa*, growing the cultures under appropriate conditions and harvesting them, followed by washing with centrifugation to yield a washed cell pellet;

(b) resuspending the washed cells in an appropriate buffer followed by disruption of the cells;

(c) centrifuging to remove cell debris and obtaining the supernatant containing soluble cell proteins;

(d) subjecting the solution obtained to anion exchange chromatography with a sodium chloride gradient elution, and pooling the fractions corresponding to each separate peak;

(e) purifying protein fractions by SDS-PAGE using a 10% T-1.42% C acrylamide-N,N-methylenebisacrylamide separating gel with a 4% T-0.36% C acrylamide-N,N-methylenebisacrylamide stacking gel polymerised in a 28 mm (internal diameter) column, run using 1% (w/v) SDS, 0.025M Tris, 0.2 M glycine buffer pH 8.3 in the upper and lower chambers at 40 mA and 10 W for 14 hours and eluting the proteins eluted using an elution buffer of 0.025 M Tris, pH 8.3 and 6 ml fractions collected at flow rate of 1 ml/min; and (f) selecting a fraction containing a protein having a molecular weight of 20 kDa or 40 kDa and isolating the protein from the selected fraction.

Alternatively the proteins may be prepared by expressing the appropriate DNA.

In addition to the treatment or prophylaxis of infection by *P. aeruginosa*, the proteins of the present invention are also of use in the diagnosis of such infection. Thus, a further aspect provides a method of detecting and/or diagnosing *P. aeruginosa* which comprises:

(a) bringing into contact with a sample to be tested one or more antigens selected from the group consisting of antigenic proteins as defined above and/or antigenic fragments thereof; and (b) detecting the presence of antibodies to *P. aeruginosa*.

In a further aspect of the invention, there is provided the use of the protein, or a nucleic acid encoding the protein, in the preparation of an agent for the treatment, prophylaxis or diagnosis of infection by *P. aeruginosa*, wherein the protein is derived from *P. aeruginosa* and either:

i) has a molecular weight of about 13 kDa as determined by SDS PAGE under reducing conditions and has the following amino terminal sequence:

```
                                          (SEQ ID NO: 1)
     A    E    T    I    V    N    T    T    K    A
     Ala  Glu  Thr  Ile  Val  Asn  Thr  Thr  Lys  Ala
``` or an antigenic fragment or a homologue thereof; or ii) has a molecular weight of about 20 kDa as determined by SDS PAGE under reducing conditions and has the following amino terminal sequence:

```
     S    T    I    E    E    R    V    K    K    I    V    A    E    Q    L
     Ser  Thr  Ile  Glu  Glu  Arg  Val  Lys  Lys  Ile  Val  Ala  Glu  Gln  Leu   (SEQ ID NO: 4)
``` or an antigenic fragment or a homologue thereof; or iii) has a molecular weight of about 40 kDa as determined by SDS PAGE under reducing conditions and has the following amino terminal sequence:

```
     M    R    H    G    D    I    S    S    S    N    D    T    V    G
     Met  Arg  His  Gly  Asp  Ile  Ser  Ser  Ser  Asn  Asp  Thr  Val  Gly   (SEQ ID NO: 5)
``` or an antigenic fragment or a homologue thereof; or iv) has a molecular weight of about 45 kDa as determined by SDS PAGE under reducing conditions and has the following amino terminal sequence:

```
M   R   A   E   L   N   Q   G   L   I   D   F   L   K   A
Met Arg Ala Glu Leu Asn Gln Gly Leu Ile Asp Phe Leu Lys Ala  (SEQ ID NO: 2)
``` or an antigenic fragment or a homologue thereof; or v) has a molecular weight of about 80 kDa as determined by SDS PAGE under reducing conditions and has the following amino terminal sequence:

```
M   S   E   Q   N   N   E   Q   R   S   Q   A   A
Met Ser Glu Gln Asn Asn Glu Gln Arg Ser Gln Ala Ala  (SEQ ID NO: 3)
``` or an antigenic fragment or a homologue thereof.

As already mentioned, the proteins isolated by the inventors have been shown to be antigenic and they and/or fragments thereof, can therefore be used as vaccines or agents for the treatment or diagnosis of infection by P. aeruginosa.

Thus, the invention also provides a pharmaceutical composition comprising one or more of the proteins (i) to (vi) as defined above and/or an antigenic fragment thereof together with a pharmaceutically acceptable excipient.

The composition may be a vaccine composition, in which case, it may also comprise an adjuvant. Examples of adjuvants well known in the art include inorganic gels such as aluminium hydroxide or water-in-oil emulsions such as incomplete Freund's adjuvant. Other useful adjuvants will be well known to the skilled person.

As mentioned above, the proteins isolated by the inventors are antigenic and therefore the invention also provides an antibody which binds specifically to one of the proteins (i) to (vi) as defined above. The antibody may be a monoclonal or a polyclonal antibody. Techniques for the preparation of both monoclonal and polyclonal antibodies are well known to those skilled in the art.

It is well known that is possible to screen an antigenic or immunogenic protein or polypeptide to identify epitopic regions, i.e. those regions which are responsible for the protein or polypeptide's antigenicity or immunogenicity. Methods well known to the skilled person can be used to test fragments and/or homologues and/or derivatives for antigenicity. Thus, the fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a protein or polypeptide, homologue or derivative as described herein. The key issue, once again, is that the fragment retains the antigenic/immunogenic properties of the protein from which it is derived.

The protein may be administered by a variety of routes including enteral, for example oral, nasal, buccal, topical or anal administration or parenteral administration, for example by the intravenous, subcutaneous, intramuscular or intraperitoneal routes.

The form taken by the composition and the excipients it contains will, of course, depend upon the chosen route of administration. For example, oral formulations may be in the form of syrups, elixirs, tablets or capsules, which may be enterically coated to protect the protein from degradation in the stomach. Nasal or transdermal formulations will usually be sprays or patches respectively. Formulations for injection may be solutions or suspensions in distilled water or another pharmaceutically acceptable solvent or suspending agent.

In a further aspect, the present invention provides a method of vaccinating a subject against P. aeruginosa which comprises the step of administering to the subject an effective amount of a protein as defined herein.

The appropriate dosage of the protein of the present invention in a vaccination will be about 5-100 microgram when administered parenterally. However the dosage will be 10-100 fold higher for nasal and oral administration, depending on the formulation, adjuvant, patient profile, etc.

As those skilled in the art will appreciate, antigenic fragments of the proteins described above may be used in any of the applications described above for the full-length proteins.

Preferred features of each aspect of the invention are as for each aspect, mutatis mutandis. The prior art documents mentioned herein are incorporated by reference to the fullest extent permitted by law.

The invention will now be described in greater detail with reference to the following examples and to the drawings in which:

BRIEF DESCRIPTION OF THE DRAWINGS

FIG. 2 shows the SDS-PAGE analysis of peak fractions from anion exchange chromatography of the crude ZWITTERGENT® extract of P. aeruginosa. Corresponding fractions from successive chromatography runs were pooled. Protein was separated on a gradient 10-15% polvacrylamide gel and Coomassie stained. Lanes: 1, molecular mass standards (values in kDa on left); 2, peak one; 3, peak two; 4, peak three; 5, peak four; 6, peak five; 7, peak six; 8, peak seven.

Figure 1:
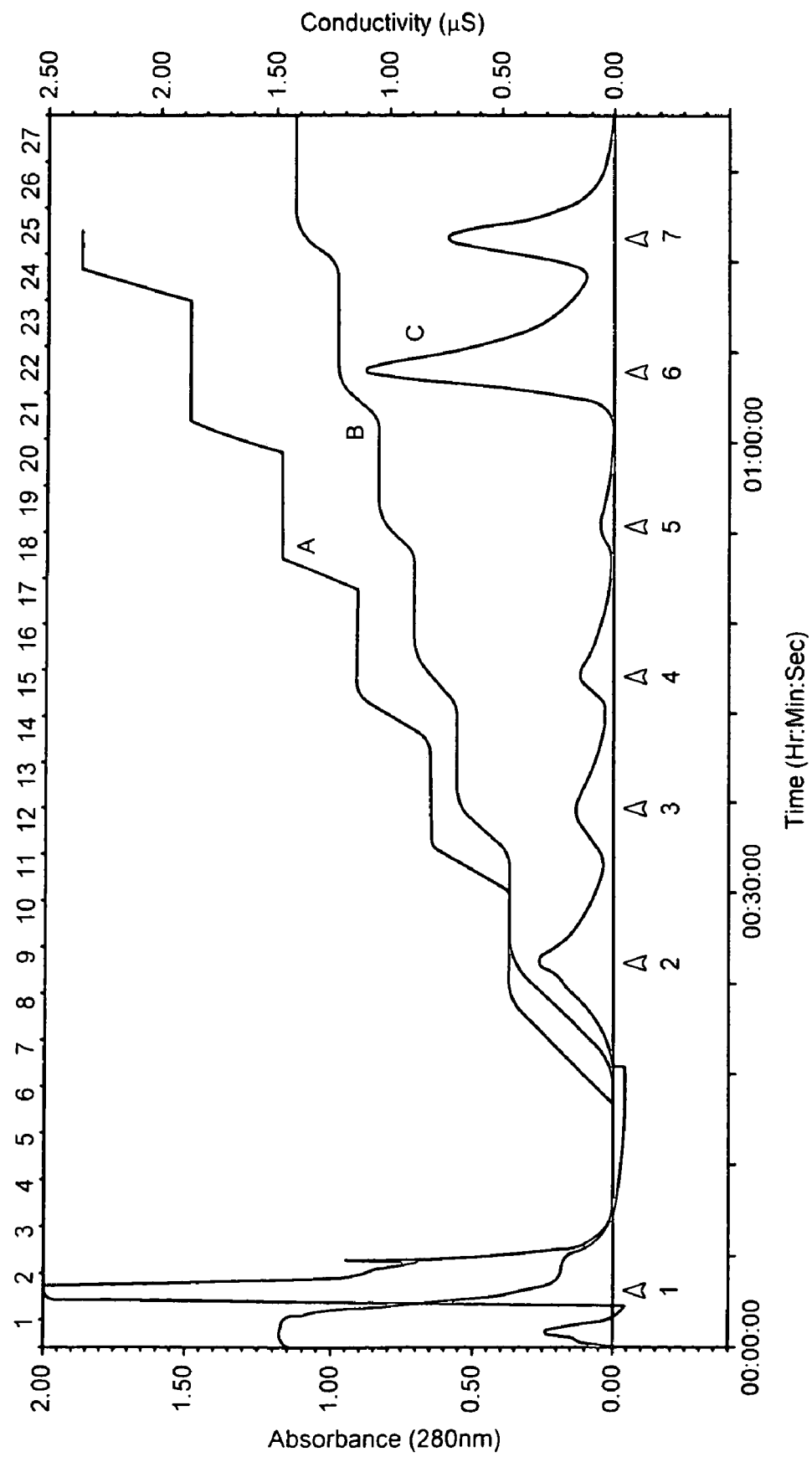
FIG. 1 shows the elution profile of P. aeruginosa proteins from crude ZWITTERGENT® extracts by anion exchange chromatography. The first peak is the unbound fraction. 'A' represents the programmed NaCl gradient, 'B' the actual NaCl gradient and 'C' represents the absorbance at 280 nm. Arrows represent separate protein peaks.

A: anti-Pa13; B: anti-Pa20 (ACP); C: anti-Pa40 (amidase); D: anti-Pa45; E: anti-Pa80.

FIG. 7 shows the DNA (SEQ ID NO: 6) and translated amino acid sequence (SEQ ID NO: 7) for Pa40.

FIG. 8 shows the DNA (SEQ ID NO: 8) and translated amino acid sequence (SEQ ID NO: 9) for Pa45.

EXAMPLE 1

Isolation of Proteins from *P. aeruginosa*

Bacterial Strains

The mucoid *P. aeruginosa* isolate Strain 385, Serotype 2 was used for the purification, for immunisation and homologous challenge. This strain was originally isolated from a chronically infected patient with cystic fibrosis. Bacterial stocks were stored at −85° C. in nutrient broth (Oxoid Unipath Ltd, Basingstoke, Hampshire, UK) and supplemented with 10% glycerol (v/v).

Bacterial Growth Conditions

Two hundred nutrient agar plates (Oxoid Unipath Ltd. Basingstoke, Hampshire, UK) were used for each extraction. Bacteria were streaked onto agar plate for lawn growth and incubated overnight at 37° C. Bacteria were harvested by scraping and washed three times by centrifugation (12000×g, 14 minutes, 4° C., Beckman Centrifuge). Following each centrifugation step, the bacterial pellet was retained and then resuspended in fresh sterile phosphate buffered saline (PBS).

Protein Purification

The washed bacterial pellet was resuspended in 20 ml of 1M sodium acetate and 1 mM β-mercaptoethanol, pH 4. The suspension was stirred at room temperature for 45 minutes before addition of 80 ml of 500 mM calcium chloride, 5% w/v of ZWITTERGENT® 3-14 (Calbiochem, Alexandria, NS, Australia). This was left to stir at room temperature for 90 min before the addition of 20% (v/v) absolute ethanol. The solution was left at 4° C. for two hours. The suspension was centrifuged at 17000×g for 15 minutes and 4° C., and the supernatant adjusted to a final concentration of 80% (v/v) ethanol. This solution was kept at 4° C. overnight. The solution was centrifuged at 17000×g for 25 minutes at 4° C. and the protein pellet resuspended in 30 ml of Buffer Z (5% ZWITTERGENT® 3-14 (w/v), 50 mM Tris and 0.01 M EDTA, pH 8.0) and incubated at room temperature for 45 minutes. The solution was centrifuged at 12000×g for 15 minutes at 4° C., the supernatant retained and dialysed overnight against distilled water at 4° C. The crude protein extract was frozen to −70° C. and lyophilised.

Anion Exchange Chromatography

Anion exchange chromatography was conducted using the Bio-scale Q2™ and Q5™ columns (Bio-Rad). The columns were MP 10 support matrix derivatised with strongly basic quaternary ammonium groups ($—N^+(CH_3)_3$) to promote binding of negatively charged proteins. The column was equilibrated with 20 ml of Buffer A (20 mM Tris-HCl, pH 8.5) at a flow rate of 2 ml/min. Lyophilised crude protein extract was resuspended in Buffer A to a concentration of <5 mg/ml (Q2) or <20 mg/ml (Q5). Proteins were eluted from the column by introducing an increasing concentration of buffered sodium chloride (Buffer B, 20 mM Tris-HCl, pH 8.5, 500 mM sodium chloride) at a flow rate of 1 ml/min. Peak apex fractions were dialysed overnight, frozen to −70° C. and lyophilised for analytical SDS-PAGE. Fractions corresponding to different peaks were pooled separately for further purification.

Purification Using SDS-Preparative Polyacrylamide Gel Electrophoresis

Partially purified proteins were further purified by using preparative polyacrylamide gel electrophoresis. Pooled fractions from the anion exchange column were lyophilised, resuspended in a minimal amount of distilled water and further dissolved in four times the amount of SDS reducing buffer (62.5 mM Tris, pH 6.8; 10% v/v glycerol; 2% w/v SDS; 5% v/v β-mercaptoethanol; 1.2×10-3% w/v bromophenol blue). This preparation was incubated at 37° C. for at least 30 minutes prior to being loaded onto the stacking gel of the electrophoresis column.

Preparative SDS-PAGE was performed with a Bio-Rad 491 Prep Cell with a 20-mil 10% T-1.42% C acrylamide-N,N-methylenebisacrylamide separating gel with a 10-ml 4% T-0.36% C acrylamide-N,N-methylenebisacrylamide stacking gel polymerised in a 28 mm (internal diameter) column. Stacking and resolving gels were prepared from 30%/2.67 w/v acrylamide/bis-acrylamide monomer stock solution (Bio-Rad). Proteins were run using 1% (w/v) SDS, 0.025M Tris, 0.2 M glycine buffer pH 8.3 in the upper and lower chambers. Running conditions were 40 mA and 10 W for 14 hours. Proteins were eluted using 0.025 M Tris, pH 8.3 and 6 ml fractions collected at flow rate of 1 ml/min. Collected fractions were frozen to −70° C., lyophilised and every fifth fraction analysed using SDS-PAGE. Identified sequential fractions containing the same protein were then pooled.

Electro-Elution

Electro-elution was substituted for preparative gel electrophoresis for some purifications. Crude protein or partially purified fractions were separated by electrophoresis using the Protean II™ xi cell (Bio-Rad) and a vertical slab electrophoresis set up. Electrophoresis was carried out using a 10% T-1.42% C acrylamide-N,N-methylenebisacrylamide separating gel with a 4% T-0.36% C acrylamide-N,N-methylenebisacrylamide stacking gel polymerised in a 16 cm (w)× 16 cm (h) and 1.0 mm (d) unit. Electrophoresis was carried out at 16 mA during migration through the stacking gel and 24 mA for separation in the resolving gel.

Elution of the protein bands from the slab gel was achieved with a whole Gel Eluter™ (Bio-Rad). Elution was performed in a transverse direction through the thickness of the gel for 45 min at 250 mA. Proteins eluted into narrow chambers were harvested under vacuum into 12 mm×75 mm tubes.

SDS Removal

Protein isolated under electrophoresis conditions contained SDS, which was subsequently removed. This involved addition of potassium phosphate to a concentration of 20 mM to concentrated protein fractions. Samples were left on ice for 60 min and the precipitated SDS was removed by centrifugation for 20 min at 6000×g and 4° C. The samples were desalted by dialysis.

Fraction Analysis

Fractions from both liquid column chromatography and preparative gel electrophoresis or electroelution were assessed for protein content by analytical SDS-PAGE and silver or Coomassie staining. The presence of the proteins of interest in particular eluted fractions was confirmed by staining analytical SDS-PAGE gels. Fractions that contained only a homogeneous (single) band were pooled and the protein concentration determined using the Pierce Micro BCA™ protein assay reagent and the Pierce™ albumin standard (Laboratory Supplies, Marrickville, NSW, Australia).

Analytical SDS-PAGE

SDS-PAGE was carried out essentially as described by Laemmli to analyse fractions for the presence of the protein of interest. A 10 ul-fraction sample was added to an equal volume of sample buffer containing SDS and Dithiothreitol (DTT) and boiled for 5 min. Electrophoresis was performed with mini-gels with a gradient of 10 to 15% by using the Biorad™ system. Molecular weight markers (Pharmacia) were run on the same mini-gels for determination of the molecular masses of the proteins.

SDS Removal

This method involved the addition of potassium phosphate to a concentration of 20 mM to concentrated protein samples. Samples were then left on ice for 60 min. The precipitated SDS was removed by centrifugation for 20 min at 6,000 g at 4° C. using dialysis against distilled water.

Staining of Polyacrylamide Gels

Analytic SDS-PAGE was followed by either Coomassie or silver staining. Gels were stained for 60 min in Coomassie staining solution, which comprised 1.0 g of Coomassie Blue R-250 stain (BioRad™), dissolved in 400 ml of methanol, 100 ml acetic acid and 50 ml of deionised water. Destaining was carried out overnight in destaining solution of 400 ml of methanol, 100 ml acetic acid and 500 ml of deionised water.

Silver staining involved the fixation of gels in 30% methanol, 10% acetic acid and formaldehyde for 4 hours. After rinsing with 50% ethanol, pre-treatment of gels was carried out with 0.8 mM sodium thiosulphate for 1 min. Three water rinses followed, then incubation in silver impregnation for 20 min. After two more water rinses, incubation in developmental solution (18% sodium carbonate, formaldehyde and sodium thiosulphate) was carried out. The reaction was stopped with a solution of 50% methanol and 12% acetic acid.

Protein Concentration Determination

Protein concentration was determined with the Pierce Micro BCA protein assay reagent and the Pierce albumin standard (Laboratory Supplies, Manickville, NSW, Australia).

Measurement of Lipopolysaccharide

The presence of lipopolysaccharide (LPS) was assessed by both silver staining of SDS-PAGE gels and assaying with E-TOXATE Limulus lysate test (Sigma, St Louis, Mo. USA).

Results

Figure 3:
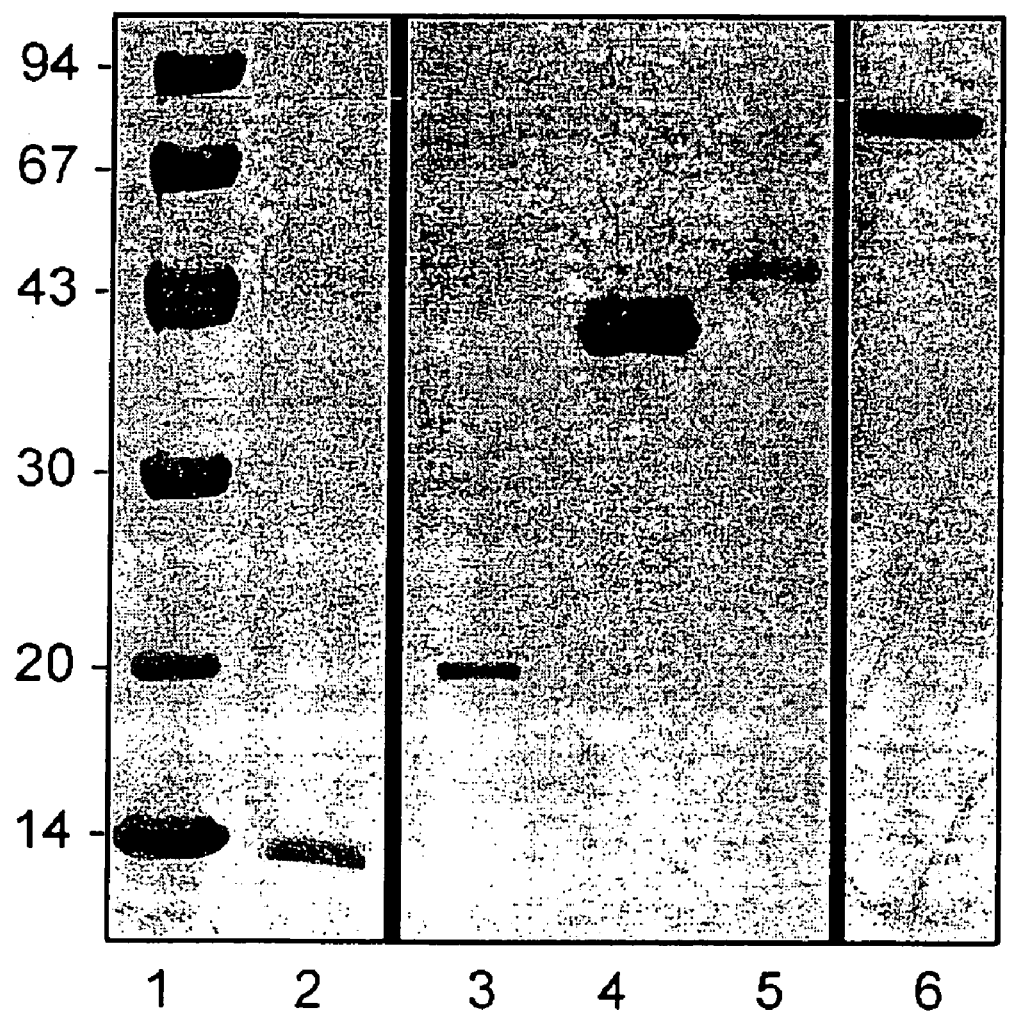
FIG. 3 shows the results of SDS-PAGE analysis of purified P. aeruginosa antigens. Samples were analysed on a 4-15 polyacrylamide gel and Coomassie stained. Lanes: 1—molecular mass standard (values on left in kDa); 2—Pa13; 3—Pa20 (ACP); 4—Pa40 (amidase); 5—Pa45; 6—Pa80.

FIG. 1 shows the elution profile of the *P. aeruginosa* zwittergent extract by anion exchange chromatography. Seven peaks are clearly visible. The first 5 peaks were pooled separately and analysed by SDS-PAGE and the molecular weights of the proteins were determined. (FIG. 2) Proteins were further purified by preparative electrophoresis for immunisation studies as discussed in Example 4. FIG. 3 shows the SDS-PAGE analysis of the purified proteins used for immunisation studies.

EXAMPLE 2

Purification of Pa80

Purification protocols to isolate quantities of protein sufficient for use in immunisation studies were developed for proteins from *Pseudomonas aeruginosa*. A three-stage process of Zwittergent detergent extraction, liquid column chromatography and preparative SDS-PAGE was utilised for separation. The antigen Pa80 was purified from *P. aeruginosa* 385 (serotype 2). SDS-PAGE confirmed the homogeneity of the purified sample. Pa80 (80 kDa) was isolated, confirmed free from the endotoxin contamination and thus suitable for investigation of its vaccine potential.

Materials and Methods

Bacteria from *P. aeruginosa* strain 385 (serotype 2) were used to purify Pa80 for immunisation studies. Bacteria were grown overnight, harvested, washed, and a crude detergent-extractable protein preparation was obtained as previously described (example 1). The lyophilised crude extract was resuspended in a minimal amount of distilled water and SDS-reducing buffer. Purification of Pa80 was carried out by anion exchange chromatography and preparative SDS-PAGE. Western and dot blotting were carried out using Pa80 specific antisera. For Western blotting, a cell lysate of *P. aeruginosa* strain 385 was separated by electrophoresis using a 10-20% gradient polyacrylamide gel by analytical SDS-PAGE and transferred to a nitrocellulose membrane (BioRad™) using a semi-dry transfer apparatus (BioRad™). After blocking in 1% w/v skim milk in Tris buffered saline (TBS) for 60 min, the membrane was incubated with a 1/1000 dilution of pooled immune sera for 90 min at room temperature. The membrane was then washed with TBS and 0.05% Tween® 20 (TTBS) and incubated in a 1/1000 dilution of horse radish peroxidase (HRP) conjugated anti IgG for 90 min. The blot was developed using HRP development reagent (BioRad™) and scanned using a GS570 densitometer (BioRad™). Dot blot of Pa385 (serotype 2) cell lysate was applied directly to the nitrocellulose membrane. Following steps were as per Western blotting.

Results

Purification of Pa80 by ZWITTERGENT® Extraction

Figure 4:
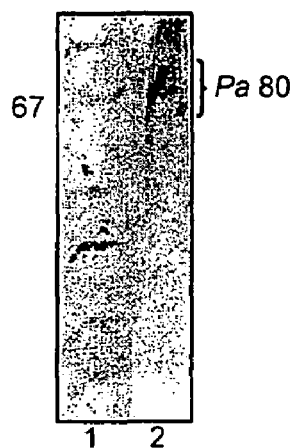
FIG. 4 shows a Western blot demonstrating the recognition of Pa80 in P. aeruginosa (strain 385) cell lysate by antigen specific antisera. Lanes (1) molecular weight markers; (2) Anti-Pa80 rat serum recognition of a 80 kDa band in the P. aeruginosa crude cell lysate.
Figure 5:
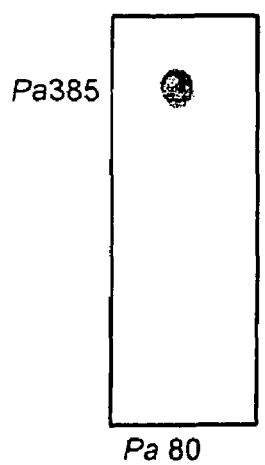
FIG. 5 shows a Dot blot of P. aeurginosa 385 (serotype2) cell lysate demonstrating recognition of Pa80 by antigen-specific antisera.

This study demonstrated the immune recognition of Pa80 within a cell lysate using Pa80-specific antisera. (FIG. 4 and FIG. 5)

Purification of Pa80 Using Anion Exchange Chromatography

Crude protein from the ZWITTERGENT® extraction was further separated using anion exchange chromatography. Bio-scale Q2 column (BioRad™) resolved the complex extract, generally, into seven separate protein peaks (FIG. 1). Pa80 appeared within the fifth peak and was identified by molecular weight on SDS-PAGE (FIG. 2). Conditions for the elution of Pa80 from the anion column were 80% Buffer A (20 mM Tris pH 8.5) with 20% Buffer B (1.5 M NaCl, 20 mM Tris, pH 8.5), UV (AU) 0.228, conductivity (mS/cm) 0.674.

Purification of Pa80 Using Preparative SDS-PAGE

Proteins were further purified from fractions containing Pa80 under denaturing conditions using both the BioRad Prep cell model 491 and the Protean II preparative SDS-PAGE.

The presence of LPS contamination was assessed by inspection of silver-stained gels and was considered absent. Quantisation using the E-TOXATE Limulus lysate test was found to be less than the level of detection for all preparations (limit 0.015 EU/ml).

TABLE 1

Yields of Pa80 from each extraction of *P. aeruginosa* (strain 385)

| Protein Code | Average yield per extract | % Yield | Total yield |
| --- | --- | --- | --- |
| Pa80 | 37 μg | 0.08% | 110 μg |

Discussion

Identification of Pa80

Pa80 has been purified to homogeneity using a combination of ZWITTERGENT® extraction and anion exchange chromatography. This protein is recognised by serum from immunised rats and shown to be protective against a live *P. aeruginosa* challenge to the lungs (See example 4). This protein represents a previously untested antigen for immunisation against *P. aeruginosa* infection.

EXAMPLE 3

Sequencing of Purified Proteins

Both NH$_2$-terminal and internal amino acid sequence analyses were carried out at the Biomolecular Resource Facility, Centre for Molecular Structure and Function, Australian National University and at the University of Liverpool U.K. for Pa80. Sequencing was carried out using the SDS-PAGE compatible S-2-carboxamidoethylation method. The alkylation reaction was performed on the protein in a solution of 10% glycerol (v/v), 5% (w/v) SDS, 0.25M Tris HCl, 100 mM 1,4-Dithiothreitol (1,4-DTT), pH 8.3. The protein was reduced initially by incubating this mixture at 90° C. for 15 minutes. The sample was then cooled to 37° C., acrylamide added to a final concentration of 3 M and the mixture incubated under argon with light excluded for 30 to 60 min. SDS reducing buffer was added, the sample subjected to SDS-PAGE, the protein was visualised by Coomassie staining and excised from the gel. Following sequence analysis, the data obtained were subjected to BLAST search (Basic Local Alignment Search Tool; The National Center for Biotechnology Information, Bethesda, Md., USA).

For Pa 80 the sample was run on an SDS-PAGE gel and Western blotted onto PVDF. The band was cut out and placed directly onto the sequencer. N-Terminal analysis was performed by Edman Degradation.

Purification of Protein Antigens and their Identification

As described above, proteins were purified from *P. aeruginosa* 385. Protein purity was assessed by SDS-PAGE (FIG. 3) and amino acid sequencing, both of which successfully identified homogenous protein preparations. Assessment of LPS levels in protein-preparations showed no detectable levels of endotoxin as assessed by the E-TOXATE kit Limulus assay (detection limit of assay was 0.015 endotoxin units/ml).

Following N-terminal amino acid sequencing, an electronic database search of Genbank sequences and sequences posted on the internet in the PA01 database using "Entrez" was conducted in order to identify proteins (see Table 2). The Pa13 N-terminal sequence was determined to be AFETIVNT-TKA (SEQ ID NO: 1). This 10 residue sequence gave no *P. aeruginosa* match suggesting that this protein has not yet been sequenced.

The Pa20 N-terminal sequence was determined to be STIEERVKKIVAEQL (SEQ ID NO: 4), which gave a 100% identity in a 15 amino acid overlap with acyl carrier proteins from *Pseudomonas aeruginosa* (DDBJ/EMBL/GenBank Accession No. 054439) and *Pseudomonas syringae* (DDBJ/EMBL/GenBank Accession No P80923).

The Pa40 N-terminal sequence was determined to be MRHGDISSSNDTVG (SEQ ID NO: 5), which gave 100% identity in a 14 amino acid overlap with amidase from *P. aeruginosa* (DDBJ/EMBL/GenBank Accession Nos. P11436 and M27612).

The Pa45 N-terminal sequence was determined to be MRAELNQGLIDFLKA (SEQ ID NO:2).

The Pa80 N-terminal sequence was determined to be MSEQNNEQRSQAA (SEQ ID NO: 3).

TABLE 2

Identification by Amino Acid Sequencing of the N-terminal of Protein Antigens Purified from *P. aeruginosa* Strain 385

| Code | Identification | kDa | Amino Acid Sequence |
|------|---------------|-----|---------------------|
| Pa13 | Unknown | 13 | AETIVNTTKA (SEQ ID NO: 1) |
| Pa20 | ACP | 20 | STIEEVKKIVAEQL (SEQ ID NO: 4) |
| Pa40 | Amidase | 40 | MRHGDISSSNDTVG (SEQ ID NO: 5) |
| Pa45 | Unknown | 45 | MRAELNQGLIDFLKA (SEQ ID NO: 2) |
| Pa80 | Unknown | 80 | MSEQNNEQRSQAA (SEQ ID NO: 3) |

EXAMPLE 4

Bacterial Clearance Following Immunisation in a Rat Model

Specific pathogen free male DA rates received an intra-Peyer's patch (IPP) immunisation on Day 1 of the experiment, an intra-tracheal (IT) boost on Day 14 and the live bacterial challenge on Day 21. The animals were sedated by anaesthesia. The small intestine was exposed through a midline abdominal incision and the antigen injected subserosal to each Peyer's patch using a 27-gauge needle. The immunisation protein was prepared by emulsification of 100 or 200 µg of protein per ml (for a total inoculum of 5 of 10 µg per rat, respectively) in a 1:1 ratio of Incomplete Freund's adjuvant (IFA) and phosphate buffered saline (PBS). At day 14 post IPP immunisation, animals received an IT boost of either 5 or 10 µg protein in 50 µl PBS. At day 21 post IPP immunisation, the animals were challenged for 4 hours with live *P. aeruginosa* (bacteria count 5×10$^8$ CFU). Bacteria were grown overnight at 37° C. in 5% CO$_2$ on nutrient agar plates, recovered, washed and resuspended in PBS to the required concentration. Protein for the IT boost or bacteria for the challenge were introduced into the lungs of sedated rats via a cannula inserted orally into the trachea. Following bacterial challenge, the animals were euthanased at 4 hours. Blood was collected and aliquots of serum stored at −20° C. for antibody analysis. Lungs were lavaged by flushing with 5×2 ml of PBS and the pooled lavage (BAL) assessed for bacteria numbers. Following lung lavage, the lungs were removed, homogenised and assessed for numbers of bacteria. The experiment was carried out with all of the proteins isolated in Example 1. However, results are presented only for those proteins which showed a protective effect.

Results—Effect of Immunisation on Pulmonary Clearance

Table 3 shows the dosages for primary IPP and secondary IT immunisations and the number of animals treated (N). Table 4 shows the bacterial clearance levels obtained in immunised and control rats. Results demonstrate significant differences in the level of clearance in both the BAL and lung homogenates except for the recovery in the group immunised with Pa20 (ACP), which did not reach statistical significance, although the bacterial load was reduced.

TABLE 3

Concentration of Purified Protein Used for IPP and IT Immunisation

| Code | Identification | N | IPP (μg) | IT (μg) |
|---|---|---|---|---|
| Pa13 | Unknown | 6 | 10 | 5 |
| Pa20 | ACP | 6 | 10 | 10 |
| Pa40 | Amidase | 5 | 5 | 5 |
| Pa45 | Unknown | 5 | 10 | 5 |
| Pa80 | Unknown | 5 | 5 | 5 |

TABLE 4

Live Bacteria Recovered from rats immunised with Protein Antigens and Challenged Post immunisation with Live *Pseudomonas aeruginosa*

| | | CFU ($log_{10}$) of *P. aeruginosa* at 4 hr post challenge | |
|---|---|---|---|
| Rat Group | N | BAL | Lung Homogenate |
| Non inimune | 11 | 8.22 ± 0.08 | 9.14 ± 0.09 |
| Pa13 | 6 | 7.64 ± 0.15 | 8.66 ± 0.11 |
| Pa20 (ACP) | 6 | 7.82 ± 0.08 | 8.75 ± 0.19 |
| Pa40 (Amidase) | 5 | 7.46 ± 0.18 | 8.67 ± 0.18 |
| Pa45 | 5 | 7.21 ± 0.21 | 8.42 ± 0.25 |
| Pa80 | 5 | 7.21 ± 0.13 | 8.31 ± 0.31 |

In Table 4, the values shown for CFU ($log_{10}$) of *P. aeruginosa* at 4 hr post challenge are means±the standard errors of either BAL fluid or lung homogenate of rats at 4 hours post homologous pulmonary challenge with live *P. aeruginosa*.

The BAL values for Pa40 (amidase), Pa45 and Pa80 are significantly different from the non immune group at $p<0.01$.

The BAL value for Pa13 and the lung homogenate values for. Pa13, Pa20 (ACP), Pa40 (amidase), Pa45 and Pa80 are significantly different from nonimmune and single immunisation groups at $p<0.05$.

EXAMPLE 5

Flow Cytometry

*P. aeruginosa* strain 385 was grown to mid logarithmic phase in nutrient broth and harvested by centrifugation at 1000×g for 10 min at 4° C. The bacteria were then incubated at 37° C. for 1 hour with a 1:50 dilution (in PBS) with either non-immune serum, immune sera or PBS. The cells were centrifuged, the supernatant removed and the bacteria resuspended in 200 μL of fluorescein isothiocyanate conjugated with anti-rat IgG diluted 1:50 in PBS. Following incubation for 30 min at 37° C., 1.8 ml of PBS was added and the bacterial cells were analysed by flow cytometry (Coulter ZL-MCL). A total of 20000 cells were counted and the data acquired in the instrument status of logarithmic mode for forward scatter, side scatter and fluorescence.

Results

Figure 6:
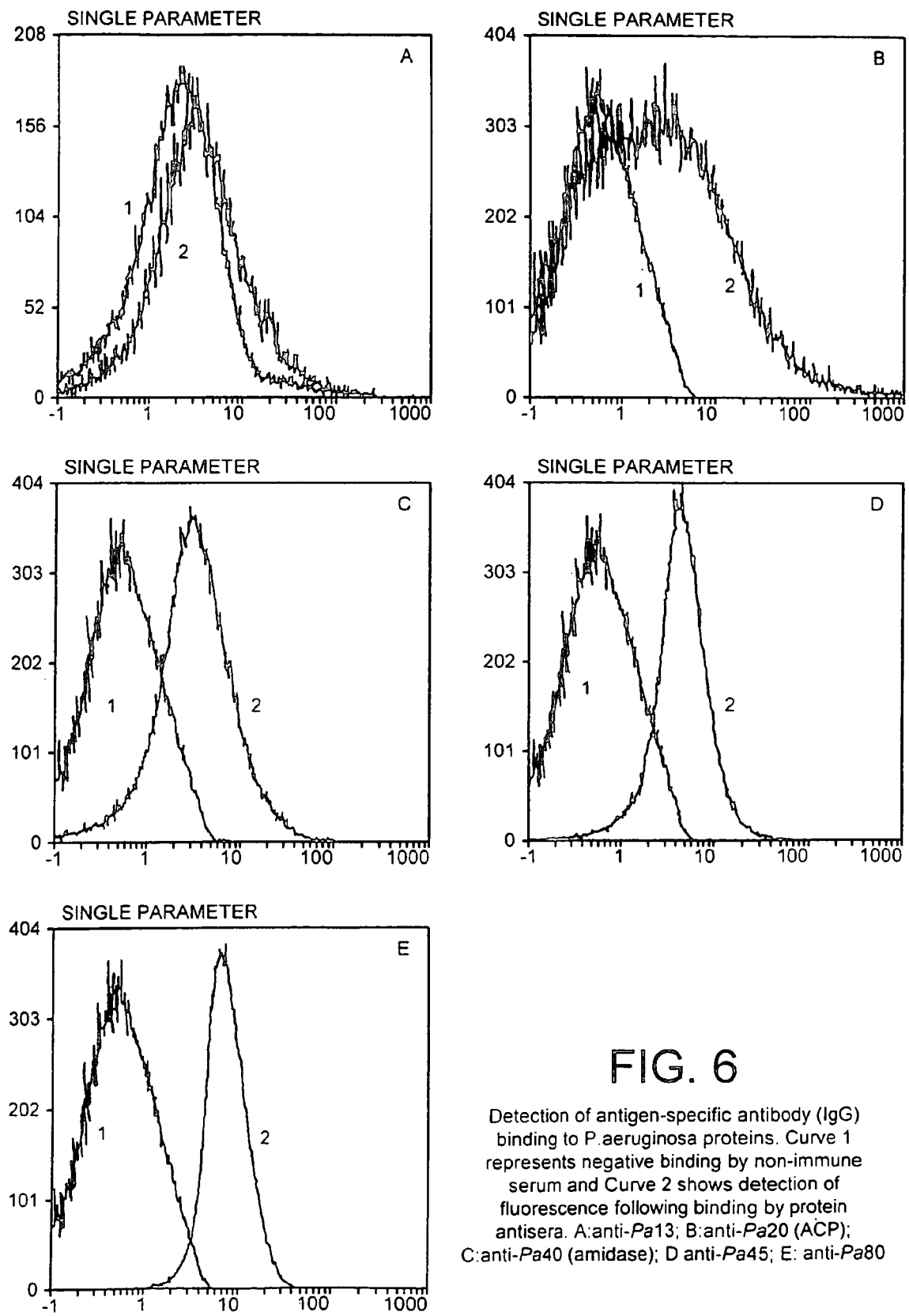
FIG. 6A to 6E shows graphs of counts (vertical axis) and log fluorescence (horizontal scale) for detection of antigen-specific antibody (IgG) binding to P. aeruginosa. Curve 1 represents negative binding by non-immune serum and Curve 2 shows detection of fluorescence following binding by protein antisera.

Non-immune rat sera was used as a control and showed no non-specific binding to *P. aeruginosa* (curve 1 in FIG. 6). The degree of binding of antisera from protein immunised rats is shown in Curve 2 FIG. 6. The degree of binding is determined by the degree of curve shift for fluorescence to the right in the graph. Thus, anti-Pa13 showed no surface binding, whereas anti sera to Pa20 (ACP), Pa40 (amidase), Pa45 and Pa80 showed significant surface binding to *P. aeruginosa*.

EXAMPLE 6

Cloning of the Pa40 and Pa45 Genes

Purification of *Pseudomonas aeruginosa* Pa385 Chromosomal DNA.

*P. aeruginosa* were grown as described in Example 1. Bacteria were washed in 30 ml PBS and recovered by centrifugation at 4,000 rpm for 10 min and the procedure repeated. The washed pellet was resuspended in 10 ml of 50 mM Tris HCl with 0.4 ml of 0.4 M EDTA and incubated at 37° C. for 20 min. 0.4 ml of 20 mg lysozyme/ml was then added and the mixture incubated for a further 10 min at 37° C. before the addition of 540 μg Proteinase K, 0.4 ml of 10% w/v SDS and 10 μg of 10 mg Ribonuclease A/ml. The mixture was then incubated at 37° C. for 2 hours or until the suspension was clear. For the first extraction, 8 ml phenol, saturated with 10 mM Tris-HCL and 1 mM EDTA was mixed for 30 seconds at 37° C. and the DNA phase extracted. For the second extraction, the DNA phase was transferred to a second tube containing 5 ml of phenol/chloroform/isoamyl alcohol (25:24:1) and mixed on ice for 30 seconds. The mixture was then centrifuged at 8,000 rpm for 15 min at 4° C. For the third extraction, the DNA phase was removed to a tube containing 5 ml chloroform/isoamyl alcohol (24:1) and centrifuged at 8,000 rpm for 15 min at 4° C. The fourth extraction repeated steps for the third extraction. The DNA was the precipitated out using 2 volumes of cold absolute ethanol. The spooled DNA was dipped into 70% v/v ethanol and suspended in 1-2 ml of TE buffer and stored at 4° C.

Oligonucleotide Design.

Site directed cloning was chosen to ensure correct orientation into the reading frame. Maximising GC content, oligonucleotides were obtained from GIBCO BRL custom primers (Life Technologies, Rockville, Md.) and were designed as follows:

Pa40BF, the 5' oligonucleotide coded for the commencement of the amidase gene. Sequence (5' to 3') GGC GGA TCC CGT CAC GGC GAT ATT TCC AGC AGC A (SEQ ID NO:10). This oligonucleotide was 34-mer in length and incorporated into BamH1 restriction site. Coupling efficiency was estimated to be 99% and the GC content 61%.

Pa40HR, the 3' oligonucleotide coded for the 3' end of the amidase gene. Sequence (5' to 3') GGC AAG CTT GGC CTC CTT CTC CAG TCC CTC (SEQ ID NO:11). This oligonucleotide was 30-mer in length and incorporated a HindIII restriction site. Coupling efficiency was estimated to be 99% and the GC content 63%.

Pa45BF, the 5' oligonucleotide coded for the commencement of the Pa45gene. Sequence (5' to 3') GGC GGA TTC CGC GCA GAA CTC AAC CAG GGC CTG (SEQ ID NO:12). This oligonucleotide was 33-mer in length and incorporated into BamH1 restriction site. Coupling efficiency was estimated to be 99% and the GC content 67%.

Pa45HR, the 3' oligonucleotide coded for the 3' end of the Pa45 gene. Sequence (5' to 3') GGC AAG CTT GGG CAG CTC GCT GCT GGC GTA GAA (SEQ ID NO:13). This oligonucleotide was 33-mer in length and incorporated a HindIII restriction site. Coupling efficiency was estimated to be 99% and the GC content 63%.

Polymerase Chain Reaction.

PCR reaction mix consisted of 1 ng Pa DNA, 15 pmol primer (each), 7.5 μm dNTP (each) and 1U Taq DNA polymerase (QIAGEN) in a total of 50[α]reaction mix. Conditions used for amplification consisted of Cycle 1 [94° C.—3 min, 55° C.—10 s, 72° C.—15 s]×1 cycle; Cycle 2 [94° C.—10 s, 50° C.—10 s, 72° C.—15 s]×35 cycles; Cycle 3 [72° C.—5 in, 25° C.—1 min]×1 cycle, using a Corbett FTS 4000 Thermal Sequencer (Corbett research, Sydney, NSW, Australia). The size of the PCR product and any non-specific products were visually assessed by electrophoresis on a 1% agars gel.

Cloning of the Pa40 and Pa45 Gene

Following PCR, unused dNTPS were removed using the silica matrix method (Progen Industries) and recovery checked by visualising the purified product on an agarose gel. The PCR product was ligated into a pGEM T-easy vector system (Promega, USA). The ligation of the insert with the vector was carried out using T4 DNA ligase under standard conditions as recommended by the manufacturer. The sample was left at 4° C. overnight.

Ligated DNA was transformed by the $CaCl_2$ method. Competent JM109 cells were thawed on ice for 5 min and 900 μl of 0.1M $CaCl_2$ added. To each 2001 μl aliquot, 1 μl of DNA was added. A positive control plasmid without insert, and a negative control used water instead of DNA were carried out. Cells were incubated on ice for 30 min then heat shocked for 45 s at 45° C. Cells were recovered by placing into 1 ml aliquot of LB media, placed at 37° C., shaking at 150 rpm, for 1 hour. Dilution of 1:100 and 1:10 of the transformation mix (diluted in LB broth) as well as undiluted transformation mix were plated on LB agar plates containing 100 μg ampicillin/ml. The number of transformants per microgram of plasmid was then estimated.

Rapid Screening of Small Cultures.

Single colonies of transformants were selected and placed in 5 ml LB broth containing 50 μg/ml of ampicillin, X-Gal and IPTG and incubated at 37° C., 180 rpm, overnight. White colonies were checked for insert by visualisation on an agarose gel following linearisation of the vector.

Determination of DNA Sequence

The double stranded DNA from the recombinant plasmid was sequence at the University of NSW. The product for sequencing was prepared using the pUC/M13 forward or reverse primer and Big Dye Terminator mix to 3.2 pmoles primer and 100 ng template made up to a 10 μl volume using sterile water. The cycle sequence [96° C.—10 s, 50° C.—5 s, 60° C.—4 min]×25 cycles were carried out on a Corbett FTS 4000 Thermal Sequencer. Sequence analysis used DNA Strider 1.3.

Results

Sequence of Pa40 and Demonstration of Cross Strain Presence.

Sequence analysis for Pa40 from *P. aeruginosa* 385 is shown in FIG. 7 (SEQ ID NO:6 and SEQ ID NO:7). The amino acid translation of the N-terminal region of the determined nucleic acid sequence is homologous to the amino acids listed under SEQ ID No 5. that were derived from N-terminal amino acid sequencing. Pa40 gene was assessed for presence in other *Pseudomonas aeruginosa* strains and serotypes using PCR with the specific primers: Pa40BF and Pa40HR. Results demonstrate PCR product of correct size in all strains and serotypes tested (See Table 5 below).

Sequence of Pa45 and Demonstration of Cross Strain Presence.

Sequence analysis for Pa45 from *P. aeruginosa* 385 is shown in FIG. 8 (SEQ ID NO:8 and SEQ ID NO:9). The amino acid translation of the N-terminal region of the determined nucleic acid sequence is homologous to the amino acids listed under SEQ ID No. 2 that were derived from N-terminal amino acid sequencing. The Pa45 gene was assessed for presence in other *Pseudomonas aeruginosa* strains and serotypes using PCR with the specific primers: Pa45BF and Pa45HR. Results demonstrate PCR product of correct size in most strains and serotypes tested (See Table 5 below). No PCR product was obtained for serotypes Pa 373, serotype 12, serotype 14 and serotype 17.

TABLE 5

PCR analysis of the Pa40 and Pa45 gene in various serotypes and clinical isolates

| | PCR Product | |
| --- | --- | --- |
| *P. aeruginosa* Strain | Pa40 gene | Pa45 gene |
| Pa373 | + | − |
| Pa385 | + | + |
| Pa423 | + | + |
| Pa459 | + | + |
| Pa552 | + | + |
| Serotype 6 | + | + |
| Serotype 7 | + | + |
| Serotype 8 | + | + |
| Serotype 9 | + | + |
| Serotype 10 | + | + |
| Serotype 11 | + | + |
| Serotype 12 | + | − |
| Serotype 13 | + | + |
| Serotype 14 | + | − |
| Serotype 15 | + | + |
| Serotype 16 | + | + |
| Serotype 17 | + | − |

+ = presence of amplified gene
− = no PCR product

What is claimed is:

1. A vaccine composition, said composition comprising an isolated immunogenic *Pseudomonas aeruginosa* protein which has a molecular weight of about 40 kDa as determined by SDS-PAGE under reducing conditions and wherein the amino terminal sequence of said protein is the amino acid sequence set forth in SEQ ID NO: 5, said vaccine composition comprising a pharmaceutically acceptable excipient and an adjuvant and wherein said vaccine composition is capable of inducing lung clearance after pulmonary infection by homologous *Pseudomonas aeruginosa* in a subject immunized with said vaccine composition.

2. The vaccine composition of claim 1, wherein said adjuvant is an inorganic gel.

3. The vaccine composition of claim 2, wherein said inorganic gel is aluminum hydroxide.

4. The vaccine composition of claim 1, wherein said adjuvant is a water-in-oil emulsion.

5. The vaccine composition of claim 4, wherein said emulsion is incomplete Freund's adjuvant.

* * * * *

UNITED STATES PATENT AND TRADEMARK OFFICE
CERTIFICATE OF CORRECTION

PATENT NO. : 7,517,533 B2  Page 1 of 1
APPLICATION NO. : 10/148414
DATED : April 14, 2009
INVENTOR(S) : Cripps et al.

It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by 734 days Delete the phrase "by 734 days" and insert -- by 1,290 days --

Signed and Sealed this

Fourth Day of May, 2010

David J. Kappos
*Director of the United States Patent and Trademark Office*

SEQUENCE LISTING

<160> NUMBER OF SEQ ID NOS: 9

<210> SEQ ID NO 1
<211> LENGTH: 10
<212> TYPE: PRT
<213> ORGANISM: Pseudomonas aeruginosa
<220> FEATURE:
<221> NAME/KEY: misc_feature
<223> OTHER INFORMATION: N-terminal sequence

<400> SEQUENCE: 1

Ala Glu Thr Ile Val Asn Thr Thr Lys Ala
1               5                   10

<210> SEQ ID NO 2
<211> LENGTH: 15
<212> TYPE: PRT
<213> ORGANISM: Pseudomonas aeruginosa
<220> FEATURE:
<221> NAME/KEY: misc_feature
<223> OTHER INFORMATION: N-Terminal sequence

<400> SEQUENCE: 2

Met Arg Ala Glu Leu Asn Gln Gly Leu Ile Asp Phe Leu Lys Ala
1               5                   10                  15

<210> SEQ ID NO 3
<211> LENGTH: 13
<212> TYPE: PRT
<213> ORGANISM: Pseudomonas aeruginosa
<220> FEATURE:
<221> NAME/KEY: misc_feature
<223> OTHER INFORMATION: N-terminal sequence

<400> SEQUENCE: 3

Met Ser Glu Gln Asn Asn Glu Gln Arg Ser Gln Ala Ala
1               5                   10

<210> SEQ ID NO 4
<211> LENGTH: 15
<212> TYPE: PRT
<213> ORGANISM: Pseudomonas aeruginosa
<220> FEATURE:
<221> NAME/KEY: misc_feature
<223> OTHER INFORMATION: N-terminal sequence

<400> SEQUENCE: 4

Ser Thr Ile Glu Glu Arg Val Lys Lys Ile Val Ala Glu Gln Leu
1               5                   10                  15

<210> SEQ ID NO 5
<211> LENGTH: 14
<212> TYPE: PRT
<213> ORGANISM: Pseudomonas aeruginosa
<220> FEATURE:
<221> NAME/KEY: misc_feature
<223> OTHER INFORMATION: N-terminal sequence

<400> SEQUENCE: 5

Met Arg His Gly Asp Ile Ser Ser Ser Asn Asp Thr Val Gly
1               5                   10

<210> SEQ ID NO 6
<211> LENGTH: 1035
<212> TYPE: DNA
<213> ORGANISM: Pseudomonas aeruginosa
<220> FEATURE:
<221> NAME/KEY: CDS
<222> LOCATION: (1)..(1035)
<223> OTHER INFORMATION:

<400> SEQUENCE: 6 cgt cac ggc gat att tcc agc agc aac gac acc gtc gga gtg gcg gtg      48
Arg His Gly Asp Ile Ser Ser Ser Asn Asp Thr Val Gly Val Ala Val
1               5                   10                  15

-continued

| | |
|---|---|
| gtc aac tac aag atg ccg cgc ctg cac acc gcg gcg gag gtc ctg gac<br>Val Asn Tyr Lys Met Pro Arg Leu His Thr Ala Ala Glu Val Leu Asp<br>20              25                  30 | 96 |
| aac gcc cgg aag atc gcc gag atg atc gtc ggc atg aag cag ggc ctg<br>Asn Ala Arg Lys Ile Ala Glu Met Ile Val Gly Met Lys Gln Gly Leu<br>35              40                  45 | 144 |
| ccc ggc atg gac ctg gtg gtg ttc ccc gag tac agc ctg cag ggc atc<br>Pro Gly Met Asp Leu Val Val Phe Pro Glu Tyr Ser Leu Gln Gly Ile<br>50              55                  60 | 192 |
| atg tac gat ccg gcg gag atg atg gaa acc gcg gtg gcg atc ccc ggc<br>Met Tyr Asp Pro Ala Glu Met Met Glu Thr Ala Val Ala Ile Pro Gly<br>65              70              75              80 | 240 |
| gag gaa acc gag ata ttc tcc cgc gcc tgc cgc aag gcc aac gtc tgg<br>Glu Glu Thr Glu Ile Phe Ser Arg Ala Cys Arg Lys Ala Asn Val Trp<br>                85                  90                  95 | 288 |
| ggc gta ttc tcc ctc acc ggc gaa cgg cac gag gag cat ccg cgc aag<br>Gly Val Phe Ser Leu Thr Gly Glu Arg His Glu Glu His Pro Arg Lys<br>            100                 105                 110 | 336 |
| gcg ccg tac aac acc ctg gtg ctg atc gac aac aac ggc gag atc gtc<br>Ala Pro Tyr Asn Thr Leu Val Leu Ile Asp Asn Asn Gly Glu Ile Val<br>            115                 120                 125 | 384 |
| cag aag tac cgc aag atc att ccc tgg tgc ccc atc gag ggc tgg tat<br>Gln Lys Tyr Arg Lys Ile Ile Pro Trp Cys Pro Ile Glu Gly Trp Tyr<br>            130                 135                 140 | 432 |
| ccc ggt ggc cag acc tac gtc agc gaa ggg ccg aag ggc atg aag atc<br>Pro Gly Gly Gln Thr Tyr Val Ser Glu Gly Pro Lys Gly Met Lys Ile<br>145             150                 155                 160 | 480 |
| agc ctg atc atc tgc gac gac ggc aac tac ccg gaa atc tgg cgc gac<br>Ser Leu Ile Ile Cys Asp Asp Gly Asn Tyr Pro Glu Ile Trp Arg Asp<br>                165                 170                 175 | 528 |
| tgc gcg atg aag ggc gcc gag ctg atc gtg cgc tgc cag ggc tac atg<br>Cys Ala Met Lys Gly Ala Glu Leu Ile Val Arg Cys Gln Gly Tyr Met<br>            180                 185                 190 | 576 |
| tac ccg gcc aag gac cag cag gtg atg atg gcc aag gcc atg gcc tgg<br>Tyr Pro Ala Lys Asp Gln Gln Val Met Met Ala Lys Ala Met Ala Trp<br>            195                 200                 205 | 624 |
| gcc aac aac tgc tat gtg gcg gtg gcc aac gcc gcc ggc ttc gac ggc<br>Ala Asn Asn Cys Tyr Val Ala Val Ala Asn Ala Ala Gly Phe Asp Gly<br>            210                 215                 220 | 672 |
| gtg tat tcc tac ttc ggc cac tcg gcg atc atc ggc ttc gac ggt cgt<br>Val Tyr Ser Tyr Phe Gly His Ser Ala Ile Ile Gly Phe Asp Gly Arg<br>225             230                 235                 240 | 720 |
| acc ctc ggt gag tgc ggc gag gag gaa atg ggt atc cag tac gcc cag<br>Thr Leu Gly Glu Cys Gly Glu Glu Glu Met Gly Ile Gln Tyr Ala Gln<br>                245                 250                 255 | 768 |
| ctg tcg ctt tcg cag atc cgc gat gcg cgc gcc aac gat cag tcg cag<br>Leu Ser Leu Ser Gln Ile Arg Asp Ala Arg Ala Asn Asp Gln Ser Gln<br>            260                 265                 270 | 816 |
| aac cac ctg ttc aag atc ctc cac cgc ggc tac agc ggc ttg cag gcg<br>Asn His Leu Phe Lys Ile Leu His Arg Gly Tyr Ser Gly Leu Gln Ala<br>            275                 280                 285 | 864 |
| tcc ggc gat ggc gac cgg ggc ctg gcg gag tgt ccg ttc gag ttc tac<br>Ser Gly Asp Gly Asp Arg Gly Leu Ala Glu Cys Pro Phe Glu Phe Tyr<br>            290                 295                 300 | 912 |
| cgc acc tgg gtc acc gac gcc gag aag gcg cgc gag aat gtc gag cga<br>Arg Thr Trp Val Thr Asp Ala Glu Lys Ala Arg Glu Asn Val Glu Arg<br>305             310                 315                 320 | 960 |
| ctg acc cgc tcg act acc ggt gtg gcg caa tgc ccg gtc ggc cgg ctg<br>Leu Thr Arg Ser Thr Thr Gly Val Ala Gln Cys Pro Val Gly Arg Leu<br>                325                 330                 335 | 1008 |

```
ccc tac gag gga ctg gag aag gag gcc                              1035
Pro Tyr Glu Gly Leu Glu Lys Glu Ala
        340                 345

<210> SEQ ID NO 7
<211> LENGTH: 345
<212> TYPE: PRT
<213> ORGANISM: Pseudomonas aeruginosa

<400> SEQUENCE: 7

Arg His Gly Asp Ile Ser Ser Asn Asp Thr Val Gly Val Ala Val
1               5                   10                  15

Val Asn Tyr Lys Met Pro Arg Leu His Thr Ala Ala Glu Val Leu Asp
                20                  25                  30

Asn Ala Arg Lys Ile Ala Glu Met Ile Val Gly Met Lys Gln Gly Leu
            35                  40                  45

Pro Gly Met Asp Leu Val Val Phe Pro Glu Tyr Ser Leu Gln Gly Ile
    50                  55                  60

Met Tyr Asp Pro Ala Glu Met Met Glu Thr Ala Val Ala Ile Pro Gly
65                  70                  75                  80

Glu Glu Thr Glu Ile Phe Ser Arg Ala Cys Arg Lys Ala Asn Val Trp
                85                  90                  95

Gly Val Phe Ser Leu Thr Gly Glu Arg His Glu His Pro Arg Lys
                100                 105                 110

Ala Pro Tyr Asn Thr Leu Val Leu Ile Asp Asn Asn Gly Glu Ile Val
            115                 120                 125

Gln Lys Tyr Arg Lys Ile Ile Pro Trp Cys Pro Ile Glu Gly Trp Tyr
130                 135                 140

Pro Gly Gly Gln Thr Tyr Val Ser Glu Gly Pro Lys Gly Met Lys Ile
145                 150                 155                 160

Ser Leu Ile Ile Cys Asp Asp Gly Asn Tyr Pro Glu Ile Trp Arg Asp
                165                 170                 175

Cys Ala Met Lys Gly Ala Glu Leu Ile Val Arg Cys Gln Gly Tyr Met
            180                 185                 190

Tyr Pro Ala Lys Asp Gln Gln Val Met Met Ala Lys Ala Met Ala Trp
        195                 200                 205

Ala Asn Asn Cys Tyr Val Ala Val Ala Asn Ala Ala Gly Phe Asp Gly
    210                 215                 220

Val Tyr Ser Tyr Phe Gly His Ser Ala Ile Ile Gly Phe Asp Gly Arg
225                 230                 235                 240

Thr Leu Gly Glu Cys Gly Glu Glu Met Gly Ile Gln Tyr Ala Gln
                245                 250                 255

Leu Ser Leu Ser Gln Ile Arg Asp Ala Arg Ala Asn Asp Gln Ser Gln
            260                 265                 270

Asn His Leu Phe Lys Ile Leu His Arg Gly Tyr Ser Gly Leu Gln Ala
        275                 280                 285

Ser Gly Asp Gly Asp Arg Gly Leu Ala Glu Cys Pro Phe Glu Phe Tyr
    290                 295                 300

Arg Thr Trp Val Thr Asp Ala Glu Lys Ala Arg Glu Asn Val Glu Arg
305                 310                 315                 320

Leu Thr Arg Ser Thr Thr Gly Val Ala Gln Cys Pro Val Gly Arg Leu
                325                 330                 335

Pro Tyr Glu Gly Leu Glu Lys Glu Ala
        340                 345
```

-continued

```
<210> SEQ ID NO 8
<211> LENGTH: 1284
<212> TYPE: DNA
<213> ORGANISM: Pseudomonas aeruginosa
<220> FEATURE:
<221> NAME/KEY: CDS
<222> LOCATION: (1)..(1284)
<223> OTHER INFORMATION:

<400> SEQUENCE: 8
```

| | | | | | | | | | | | | | | | | |
|---|---|---|---|---|---|---|---|---|---|---|---|---|---|---|---|---|
| cgc | gca | gaa | ctc | aac | cag | ggc | ctg | gtc | gat | ttc | ctc | aag | gcc | tcg | ccc | 48 |
| Arg | Ala | Glu | Leu | Asn | Gln | Gly | Leu | Val | Asp | Phe | Leu | Lys | Ala | Ser | Pro | |
| 1 | | | | 5 | | | | | 10 | | | | | 15 | | |
| acg | cct | ttc | cat | gct | acc | gcc | agc | ctc | gcc | cgc | cgc | ctg | gaa | gcc | gcc | 96 |
| Thr | Pro | Phe | His | Ala | Thr | Ala | Ser | Leu | Ala | Arg | Arg | Leu | Glu | Ala | Ala | |
| | | | 20 | | | | | 25 | | | | | 30 | | | |
| ggc | tac | cgc | cgc | ctc | gac | gag | cgc | gac | gcc | tgg | cac | acc | gaa | gcc | ggc | 144 |
| Gly | Tyr | Arg | Arg | Leu | Asp | Glu | Arg | Asp | Ala | Trp | His | Thr | Glu | Ala | Gly | |
| | 35 | | | | | 40 | | | | | 45 | | | | | |
| ggc | cgc | tac | tac | gtg | acc | cgt | aac | gac | tcg | tcg | ctg | atc | gcc | atc | cgc | 192 |
| Gly | Arg | Tyr | Tyr | Val | Thr | Arg | Asn | Asp | Ser | Ser | Leu | Ile | Ala | Ile | Arg | |
| | 50 | | | | | 55 | | | | | 60 | | | | | |
| ctg | ggc | cgt | cgc | tcg | ccc | ctg | gaa | agc | ggc | ttc | cgc | ctg | gtc | ggc | gcg | 240 |
| Leu | Gly | Arg | Arg | Ser | Pro | Leu | Glu | Ser | Gly | Phe | Arg | Leu | Val | Gly | Ala | |
| 65 | | | | | 70 | | | | | 75 | | | | | 80 | |
| cac | acc | gac | agc | ccc | tgc | ctg | cgg | gtc | aag | ccg | aac | ccg | gag | atc | gct | 288 |
| His | Thr | Asp | Ser | Pro | Cys | Leu | Arg | Val | Lys | Pro | Asn | Pro | Glu | Ile | Ala | |
| | | | | 85 | | | | | 90 | | | | | 95 | | |
| cgc | aac | ggc | ttc | ctc | cag | ctc | ggc | gtc | gaa | gtc | tat | ggc | ggc | gcc | ctc | 336 |
| Arg | Asn | Gly | Phe | Leu | Gln | Leu | Gly | Val | Glu | Val | Tyr | Gly | Gly | Ala | Leu | |
| | | | 100 | | | | | 105 | | | | | 110 | | | |
| ttc | gcc | ccc | tgg | ttc | gac | cgc | gac | ctg | tca | ctg | gcc | ggg | cgc | gtc | acc | 384 |
| Phe | Ala | Pro | Trp | Phe | Asp | Arg | Asp | Leu | Ser | Leu | Ala | Gly | Arg | Val | Thr | |
| | | 115 | | | | | 120 | | | | | 125 | | | | |
| ttc | cgc | gcc | aat | ggc | aag | ctg | gaa | agc | cgc | ctg | gtc | gac | ttc | cgc | aag | 432 |
| Phe | Arg | Ala | Asn | Gly | Lys | Leu | Glu | Ser | Arg | Leu | Val | Asp | Phe | Arg | Lys | |
| | 130 | | | | | 135 | | | | | 140 | | | | | |
| gcc | atc | gcg | gta | atc | ccc | aac | ctg | gcc | atc | cat | ctc | aac | cgc | gcc | gcc | 480 |
| Ala | Ile | Ala | Val | Ile | Pro | Asn | Leu | Ala | Ile | His | Leu | Asn | Arg | Ala | Ala | |
| 145 | | | | | 150 | | | | | 155 | | | | | 160 | |
| aac | gag | ggt | tgg | ccg | atc | aac | gcg | cag | aac | gaa | ctg | ccg | ccg | atc | atc | 528 |
| Asn | Glu | Gly | Trp | Pro | Ile | Asn | Ala | Gln | Asn | Glu | Leu | Pro | Pro | Ile | Ile | |
| | | | | 165 | | | | | 170 | | | | | 175 | | |
| gcc | cag | ctg | gcg | ccg | ggc | gag | gcc | gcc | gac | ttc | cgc | ctg | ctc | ctc | gac | 576 |
| Ala | Gln | Leu | Ala | Pro | Gly | Glu | Ala | Ala | Asp | Phe | Arg | Leu | Leu | Leu | Asp | |
| | | | 180 | | | | | 185 | | | | | 190 | | | |
| gaa | cat | ctg | ctg | cgc | gag | cac | ggc | atc | acc | gcc | gac | gtg | gta | ctg | gac | 624 |
| Glu | His | Leu | Leu | Arg | Glu | His | Gly | Ile | Thr | Ala | Asp | Val | Val | Leu | Asp | |
| | | 195 | | | | | 200 | | | | | 205 | | | | |
| tac | gag | ctg | tcg | ttc | tac | gac | acc | cag | tcc | gcc | gcg | gtg | gta | ggt | ctc | 672 |
| Tyr | Glu | Leu | Ser | Phe | Tyr | Asp | Thr | Gln | Ser | Ala | Ala | Val | Val | Gly | Leu | |
| | 210 | | | | | 215 | | | | | 220 | | | | | |
| aac | gac | gag | ttc | atc | gcc | ggg | gcg | cgc | ctg | gac | aac | ctg | ctg | tcc | tgc | 720 |
| Asn | Asp | Glu | Phe | Ile | Ala | Gly | Ala | Arg | Leu | Asp | Asn | Leu | Leu | Ser | Cys | |
| 225 | | | | | 230 | | | | | 235 | | | | | 240 | |
| cac | gcc | ggc | ctg | gaa | gcc | ctg | ctc | aac | gcc | gaa | ggc | gac | gag | aac | tgc | 768 |
| His | Ala | Gly | Leu | Glu | Ala | Leu | Leu | Asn | Ala | Glu | Gly | Asp | Glu | Asn | Cys | |
| | | | | 245 | | | | | 250 | | | | | 255 | | |
| atc | ctg | gtc | tgc | acc | gac | cac | gag | gaa | gtc | ggt | tcc | tgt | tcg | cat | tgc | 816 |
| Ile | Leu | Val | Cys | Thr | Asp | His | Glu | Glu | Val | Gly | Ser | Cys | Ser | His | Cys | |
| | | | 260 | | | | | 265 | | | | | 270 | | | |

```
ggc gcc gac ggt ccg ttc ctc gaa cag gta ctg cgc ctg ctg ccg      864
Gly Ala Asp Gly Pro Phe Leu Glu Gln Val Leu Arg Leu Leu Pro
        275                 280                 285 gaa ggc gac gcc ttc agc cgg gcg atc cag cgc tcg ctg ctg gtc tcg  912
Glu Gly Asp Ala Phe Ser Arg Ala Ile Gln Arg Ser Leu Leu Val Ser
290                 295                 300 gcc gac aac gcc cat ggc gta cac ccg aac tac gcc gac aag cac gac  960
Ala Asp Asn Ala His Gly Val His Pro Asn Tyr Ala Asp Lys His Asp
305                 310                 315                 320 gcc aac cat ggc ccg gcg ctg aac ggc ggt ccg gtg atc aag atc aac  1008
Ala Asn His Gly Pro Ala Leu Asn Gly Gly Pro Val Ile Lys Ile Asn
                325                 330                 335 agc aac cag cgc tat gcc acc aac agc gaa acc gcc ggc ttc ttc cgc  1056
Ser Asn Gln Arg Tyr Ala Thr Asn Ser Glu Thr Ala Gly Phe Phe Arg
            340                 345                 350 cac ctc tgc cag gac agc gaa gtg ccg gtg cag agc ttc gtg acc cgc  1104
His Leu Cys Gln Asp Ser Glu Val Pro Val Gln Ser Phe Val Thr Arg
        355                 360                 365 agc gac atg gga tgc ggc tcg acc atc ggc ccg atc acc gcc agc cag  1152
Ser Asp Met Gly Cys Gly Ser Thr Ile Gly Pro Ile Thr Ala Ser Gln
370                 375                 380 gtc ggc gtg cgc acc gtc gac ata ggc ctg ccg acc ttc gcc atg cac  1200
Val Gly Val Arg Thr Val Asp Ile Gly Leu Pro Thr Phe Ala Met His
385                 390                 395                 400 tcg att cgc gag ctg gcc ggt agc cat gac ctg gcg cac ctg gtc aag  1248
Ser Ile Arg Glu Leu Ala Gly Ser His Asp Leu Ala His Leu Val Lys
                405                 410                 415 gtg ctc ggc gcc ttc tac gcc agc agc gag ctg ccc                  1284
Val Leu Gly Ala Phe Tyr Ala Ser Ser Glu Leu Pro
        420                 425

<210> SEQ ID NO 9
<211> LENGTH: 428
<212> TYPE: PRT
<213> ORGANISM: Pseudomonas aeruginosa

<400> SEQUENCE: 9

Arg Ala Glu Leu Asn Gln Gly Leu Val Asp Phe Leu Lys Ala Ser Pro
1               5                   10                  15

Thr Pro Phe His Ala Thr Ala Ser Leu Ala Arg Arg Leu Glu Ala Ala
            20                  25                  30

Gly Tyr Arg Arg Leu Asp Glu Arg Asp Ala Trp His Thr Glu Ala Gly
        35                  40                  45

Gly Arg Tyr Tyr Val Thr Arg Asn Asp Ser Ser Leu Ile Ala Ile Arg
    50                  55                  60

Leu Gly Arg Arg Ser Pro Leu Glu Ser Gly Phe Arg Leu Val Gly Ala
65                  70                  75                  80

His Thr Asp Ser Pro Cys Leu Arg Val Lys Pro Asn Pro Glu Ile Ala
                85                  90                  95

Arg Asn Gly Phe Leu Gln Leu Gly Val Glu Val Tyr Gly Gly Ala Leu
            100                 105                 110

Phe Ala Pro Trp Phe Asp Arg Asp Leu Ser Leu Ala Gly Arg Val Thr
        115                 120                 125

Phe Arg Ala Asn Gly Lys Leu Glu Ser Arg Leu Val Asp Phe Arg Lys
    130                 135                 140

Ala Ile Ala Val Ile Pro Asn Leu Ala Ile His Leu Asn Arg Ala Ala
145                 150                 155                 160
```

```
-continued

Asn Glu Gly Trp Pro Ile Asn Ala Gln Asn Glu Leu Pro Pro Ile Ile
            165             170             175

Ala Gln Leu Ala Pro Gly Glu Ala Ala Asp Phe Arg Leu Leu Leu Asp
            180             185             190

Glu His Leu Leu Arg Glu His Gly Ile Thr Ala Asp Val Val Leu Asp
            195             200             205

Tyr Glu Leu Ser Phe Tyr Asp Thr Gln Ser Ala Ala Val Val Gly Leu
            210             215             220

Asn Asp Glu Phe Ile Ala Gly Ala Arg Leu Asp Asn Leu Leu Ser Cys
225             230             235             240

His Ala Gly Leu Glu Ala Leu Leu Asn Ala Glu Gly Asp Glu Asn Cys
            245             250             255

Ile Leu Val Cys Thr Asp His Glu Glu Val Gly Ser Cys Ser His Cys
            260             265             270

Gly Ala Asp Gly Pro Phe Leu Glu Gln Val Leu Arg Arg Leu Leu Pro
            275             280             285

Glu Gly Asp Ala Phe Ser Arg Ala Ile Gln Arg Ser Leu Leu Val Ser
            290             295             300

Ala Asp Asn Ala His Gly Val His Pro Asn Tyr Ala Asp Lys His Asp
305             310             315             320

Ala Asn His Gly Pro Ala Leu Asn Gly Gly Pro Val Ile Lys Ile Asn
            325             330             335

Ser Asn Gln Arg Tyr Ala Thr Asn Ser Glu Thr Ala Gly Phe Phe Arg
            340             345             350

His Leu Cys Gln Asp Ser Glu Val Pro Val Gln Ser Phe Val Thr Arg
            355             360             365

Ser Asp Met Gly Cys Gly Ser Thr Ile Gly Pro Ile Thr Ala Ser Gln
            370             375             380

Val Gly Val Arg Thr Val Asp Ile Gly Leu Pro Thr Phe Ala Met His
385             390             395             400

Ser Ile Arg Glu Leu Ala Gly Ser His Asp Leu Ala His Leu Val Lys
            405             410             415

Val Leu Gly Ala Phe Tyr Ala Ser Ser Glu Leu Pro
            420             425
```